US006516288B2

(12) United States Patent
Bagne

(10) Patent No.: US 6,516,288 B2
(45) Date of Patent: Feb. 4, 2003

(54) METHOD AND SYSTEM TO CONSTRUCT ACTION COORDINATION PROFILES

(76) Inventor: Curtis A. Bagne, 2971 Vineyards Dr., Troy, MI (US) 48098

( * ) Notice: Subject to any disclaimer, the term of this patent is extended or adjusted under 35 U.S.C. 154(b) by 0 days.

(21) Appl. No.: 09/974,016

(22) Filed: Oct. 10, 2001

(65) Prior Publication Data

US 2002/0038195 A1 Mar. 28, 2002

Related U.S. Application Data

(63) Continuation-in-part of application No. 09/470,956, filed on Dec. 22, 1999, now Pat. No. 6,317,700.
(60) Provisional application No. 60/238,937, filed on Oct. 10, 2000.

(51) Int. Cl.[7] .............................................. G04F 10/10
(52) U.S. Cl. ........................................ 702/179; 703/11
(58) Field of Search ................................ 702/179, 181, 702/6, 27, 108, 19–21; 703/11, 17, 22; 604/890.1, 891.1, 892.2

(56) References Cited

U.S. PATENT DOCUMENTS

| | | |
|---|---|---|
| 5,251,126 A | 10/1993 | Kahn et al. |
| 5,528,516 A | 6/1996 | Yemini et al. |
| 5,640,549 A | 6/1997 | Powsner et al. |
| 5,715,451 A | 2/1998 | Marlin |
| 5,742,811 A | 4/1998 | Agrawal et al. |
| 6,051,209 A | 4/2000 | Metz et al. |
| 6,055,491 A | 4/2000 | Biliris et al. |
| 6,098,024 A | 8/2000 | Chen et al. |
| 6,134,510 A | 10/2000 | Deco et al. |
| 6,173,240 B1 | 1/2001 | Sepulveda et al. |
| 6,249,755 B1 | 6/2001 | Yemini et al. |

OTHER PUBLICATIONS

Padmanabhan, Vasantha, et al., Neuroendocrine Control of Follicle–Stimulating Hormone (FSH) Section. I. Direct Evidence For Separate Episodic and Basal Components of FSH Secretion, Endocrine, 138, 1997, pp. 424–432, 1997.
Midgley, Jr., A Rees, et al. Nonclassical Secretory Dynamics of LH Revealed By Hypothalamo–Hypophyseal Portal Sampling of Sheep, Endocrine, vol. 6. No. 2, Apr. 1997 pp. 133–143.
Ideker, Trey, et al. Integrated Genomic and Proteomic Analyses of a Systematically Perturbed Metabolic Network, Science, vol. 292, May 4, 2001, pp. 929–934.

Primary Examiner—Marc S. Hoff
Assistant Examiner—Edward Raymond
(74) Attorney, Agent, or Firm—Brooks & Kushman P.C.

(57) ABSTRACT

Action coordination profiles are part of a platform data processing technology that is distinct from but often complementary to the statistical method. It uses repeated measures or time series data to measure interactions (longitudinal associations, temporal contingencies) between and among variables or sets of variables for individuals. The interaction measures show how individual complex systems may control and regulate themselves, of how two or more individual systems may interact, of how complex systems may be controlled or affected by their environments including treatments, and of how individual systems may control or affect their environments. The systems can be object of investigation such as brains, organisms, patients, economies, investment markets, populations, machines, or processes. The actions can be physical, chemical, biological, behavioral, mental, or social. This invention can be used to help inform the process of building mathematical models. This invention also can be said to help make data speak by drawing generalized conclusions and making predictions about how individuals function and interact with their environments. Action coordination profiles and any resulting models can help advance basic and applied science.

111 Claims, 3 Drawing Sheets

METHOD AND SYSTEM TO CONSTRUCT ACTION COORDINATION PROFILES

CROSS-REFERENCE TO RELATED APPLICATION

This application is a continuation-in-part of application Ser. No. 09/470,956 that was filed on Dec. 22, 1999 now U.S. Pat. No. 6,317,700. This application claims the benefit of U.S. Provisional patent application Serial No. 60/238,937 filed Oct. 10, 2000 and entitled "Method and System to Compute Action Coordination Profiles."

BACKGROUND OF THE INVENTION

1.1. Technical Field

This invention is a method or system to construct at least one profile representing how the actions of an object of investigation are coordinated, the profile(s) being based on computed measures of longitudinal association or temporal contingency that quantify patterns of interaction in repeated measures or time series data that include two or more variables for one individual.

1.2. Description of Related Art

Scientific knowledge often is represented in the form of mathematical models. Prior art related to this invention will be described in the context of computational methods and systems to create, verify, and refine models that represent objects of investigation.

The statistical method is a primary computational method to inform the process of model building. This invention addresses certain fundamental problems that derive from limitations often encountered when the statistical method is a primary means to inform the process of creating, verifying and refining mathematical models. By addressing these problems, this invention facilitates many scientific investigations and practical arts that may benefit from scientific knowledge.

The Appendix is an outline that helps reveal the logical structure of this application.

1.2.1. The Need to Measure Interactions that are Temporal Contingencies

Model builders generally identify an object to model and abstract variables that may be relevant to its functioning. Then modelers determine how the variables interact in order to inform the process of model construction. To a large extent, mathematical models are verified by the extent to which they accurately represent interactions of their objects in the real world.

The statistical method is an important tool for constructing many mathematical models. The statistical method includes various measures and procedures for revealing interactions that can be modeled.

A primary problem addressed by this invention derives from the fact that the statistical method is best suited to address objects of investigation that are collective entities. Groups, samples, and populations are collective entities.

Section 1.2 of parent patent application Ser. No. 09/470,956 describes many limitations and problems of the prior art. Many of these problems, limitations, and solutions are illustrated in the context of clinical trials. This invention also addresses these problems and limitations but generally in the broader context of complex systems. Section 1.2.2 of this document emphasizes problems more specifically addressed by this invention. Section 2.4 of this document describes how this and the parent invention address the following problems.

1.2.2. Specific Problems Involved in the Prior Art

The statistical method and mathematical models often are used to investigate complex systems. For example, mathematical models based on statistical analyses of group data have been used to model the apparent effects of cholesterol and other lipid fractions on mortality and major cardiovascular health events. Such models serve important functions. For example, mathematical models have used laboratory data to predict the long-term health effects of new cholesterol lowering drugs. Nevertheless, statistical analyses have important limitations for investigations of complex systems.

Conventional applications of the statistical method are best suited for analyses of cross-sectional data for collective entities and for predicting events such as death that are not recurrent for individuals. Statistical analyses are not as well suited to measure longitudinal associations or temporal contingencies between and among variables within individuals—interactions that become evident in longitudinal, repeated measures, or time series data.

The statistical method does have some functionality for analyzing repeated measures data, especially for groups. For example, the statistical method often is used to analyze change scores such as pre-post differences in clinical trials. However, this functionality becomes limited as the number of repeated measurements increases. This limitation is due to the fact that the number of differences between any two measurements increases rapidly with the number of repeated measurements. In addition, it is not meaningful, appropriate or useful to conduct statistical tests on all differences that are possible when there are more than a few repeated measurements.

The statistical method also includes techniques such as repeated measures analysis of variance. However, the usefulness of such techniques tends to be limited when the levels of one or more independent variables differ across many repeated measurements for each individual. For example, generally it is not feasible with conventional analyses to substitute blood levels of drug for planned doses before rerunning analyses of the effects of treatment on health.

Conventional data analysis procedures are of limited value for supporting detailed yet comprehensive investigations of complex individual systems whose variables may interact in a nonlinear manner. Here is additional information about five problem areas that are mentioned in the preceding statement—individuality, complexity, nonlinearity, comprehensiveness, and detail—together with a statement about the need to address all these problem areas as a set in particular investigations.

1.2.2.1. Problems Involving Individuality

The statistical method is best suited for analyses of cross-sectional data for collective entities such as groups. Many statistical descriptions and inferences are about measures of central tendency for groups. Statistical analyses often are based on assignments of individuals to groups such as treated or not treated, responder or non-responder. The results of such analyses apply most directly to collective entities.

The fundamental limitation of the statistical method that involves individuality will be viewed from two perspectives: (1) the application and (2) the discovery of scientific knowledge. Both perspectives will be illustrated by example.

The statistical method often is applied to describe groups and to use sample data to make inferences about populations. Statistical inferences are used to draw generalized conclusions and make predictions. The extent to which generalized conclusions and predictions about collective entities apply to individuals generally is limited. This can be illustrated in the context of group clinical trials. Individual patients are not apt to experience the same safety and efficacy as the average patient in a clinical trial.

The extent to which generalized conclusions and predictions about populations apply to individuals depends on the extent to which individuals are typical of groups. It also depends on the extent to which samples represent populations—at least with respect to all considerations relevant to particular investigations—as well as how members of samples are assigned to treatment groups.

Science is accounting for more and more factors that affect the responses of patients to medical treatments. For example, advances in genetics are identifying many ways in which individuals differ in manners that are relevant to disease and response to treatment. People need better ways to individualize treatment.

The fundamental limitation of the statistical method with respect to individuality also has profound implications for scientific discovery. This will be illustrated in the context of functional genomics and proteomics as it involves health disorders and medical treatments.

Now that genomes are being mapped, some high priority tasks are to identify how the products of gene expression function together and to identify how genetic differences that distinguish individuals, such as single nucleotide polymorhpisms, affect biological functions and responses to treatments. Such tasks currently are hampered by a lack of methods that can be applied to individuals to measure how proteins interact to control biological functions, of how treatments affect protein interactions, and of how treatments interact with proteins and health variables. Measurement of such interactions for individuals, as distinct from groups, is becoming increasingly valuable as it becomes easier to identify how individuals differ genetically.

Group assignments and averages tend to obscure effects of genetic differences on health for individuals and their individual responses to treatments. This makes it difficult to identify genetic differences and form classifications that are predictive of health disorders and differential responses to drugs. This in turn makes it difficult to target drugs to the right patients during drug development and during clinical care.

1.2.2.2. Problems Involving Complexity

Complexity derives from the fact that individual systems often have many parts, have different types of action, and function in various and changing environments. Furthermore, certain concepts that often are applied to individuals have various manifestations. For example, health of persons is manifested at different levels of measurement hierarchies such as through laboratory measures, signs and symptoms of disorder, measures of physical and mental functioning, and measures of quality of life.

Complexity in the context of empirical investigations often becomes evident by the fact that many variables are available to describe individuals and their environments. Furthermore, many of these variables interact in various combinations. Investigators and practitioners need better methods and systems to quantify, discover, and describe many interactions simultaneously.

1.2.2.3. Problems Involving Nonlinearity

Interactions between and among variables that describe complex systems often are not linear. Two aspects of nonlinearity can be illustrated in the context of multiple linear regression, a commonly used statistical procedure for creating mathematical models. Multiple linear regression models describe the functional relationship between a dependent variable, y, and a set of dependent variables, $x_1, x_2, \ldots x_n$.

Two aspects of linearity, proportionality and additivity, can be illustrated with the equation $y=4+5x_1+2x_2$. For this equation, each one-unit increase in $x_1$ yields a 5-unit increase in y regardless of the value of $x_1$. This illustrates proportionality. Furthermore, the effects of $x_1$ and $x_2$ in this equation are additive. However, complex systems often manifest nonlinear interactions. People need improved methods and systems to address nonlinearity.

1.2.2.4. Problems Involving Comprehensiveness

A productive but conventional experimental research strategy is to isolate independent variables and investigate their effects one by one. Such research often is hypothesis driven—hypotheses that may be rejected by statistical tests based on group data for collective entities. This isolate-and-test strategy tends toward simplified models that do not reveal how many variables, parts, and manifestations of complex systems interact in coordinated manners.

The failure to measure how complex systems interact in coordinated manners is a problem because coordinated action is a hallmark of how complex systems function in interesting and important ways. We need improved methods and systems to investigate how variables, parts, and manifestations of complex systems function together to regulate and sustain themselves as whole individuals that act as agents and respond. Such methods and systems would be more comprehensive of how many variables, parts, and manifestations of individual complex systems interact.

Biology is beginning to recognize the limits of the isolate-and-test strategy. Dr. Leroy Hood and the Institute for Systems Biology advocate systems biology (http://www.systemsbiology.org/workwhat.html). They explicitly recognize that one cannot learn about biological systems by studying one gene or protein at a time. They recognize the need to study interactions within and across levels of biological information. They recognize that complex systems give rise to emergent or systems properties such as abilities of brains to learn and remember.

Dr. Hood has described this new approach to biology as "discovery science." He contributed to the initiation of the Human Genome Project—a prime example of discovery science. "Discovery science enumerates the components of particular objects independent of the questions that characterize the hypothesis-driven science commonly practiced in biology" (http://www.systemsbiology.org/workhist.html).

A recent article on the yeast galactose-utilization pathway was considered by the authors to demonstrate "proof-of-principle" of the systems approach to biology (T. Ideker, V. Thorsson, J. A. Ranish, R. Christmas, J. Buhler, J. K. King, R. Bumgarner, D. R. Goodlett, R. Aebersold, L Hood, *Science*, 292, 929–934, 2001). Although the objective of this research was "to build, test, and refine a model of a cellular pathway" using, among other things, information about protein-protein interactions, there appears to be no global or comprehensive attempt of measure the interactions using time series data on protein levels.

Although the need for comprehensive methods and systems for measuring interactions has been illustrated in the context of biology, similar problems plague investigations of many other types of complex system.

1.2.2.5. Problems Involving Detail

The need for detailed investigations becomes evident in at least two different ways. First, it often would be valuable to investigate many different variables in particular investigations. This can be illustrated with the rating scales that often are used in clinical trials for antidepressant drugs. Such composite rating scales often include many items measuring different things such as mood, movement, ideation, and sleep. There is need for more effective methods to investigate the effects of drugs both across all items and for detailed investigations of drug effects on individual items.

Second, there is need for more detailed investigations with respect to each of the individual variables that may be investigated, for example, in clinical trials. For example, it may not be enough to investigate how a particular dose of drug affects depression. There also is need to investigate treatment effects as functions of dose or blood levels of drug, episodes of treatment, as well as delay and persistence of response to treatment—both for individual patients and for groups of patients.

1.2.2.6. Need to Investigate All Five Types of Problem as a Set

Various techniques have been developed to address at least some of the problems just described. However, the prior art tends to address the particular problems individually. This piecemeal approach does not recognize that all five types of problem are of one cloth. All five types of problem need to be addressed as a set. Tradeoffs between, for example, detail and comprehensiveness for particular investigations should not be forced by the limitations of methods and systems used to process data.

Important aspects of the dynamic involving different strategies of scientific investigation can be discussed in terms of problems in this set. One example is the dynamic between comprehensive and detailed investigations. Distinctions among the sciences themselves such as chemistry, biology, and psychology can be viewed as attempts to limit the comprehensiveness of investigations. A fundamental and productive research strategy is to focus particular efforts on ever more detailed investigations of ever more delimited sets of phenomena. On the other hand, many people recognize the need to investigate complex wholes. We need better methods and systems to accommodate both strategies simultaneously.

1.2.3. Citations

U.S. Pat. No. 6,055,491 involves a method and apparatus for analyzing co-evolving time sequences.

U.S. Pat. Nos. 6,249,755 and 5,528,516 involve an apparatus and method for event correlation and problem reporting.

U.S. Pat. No. 6,173,240 presents multidimensional uncertainty analysis.

U.S. Pat. No. 6,134,510 describes a method for detecting synchronicity between several digital measurement series with the aid of a computer.

U.S. Pat. No. 6,098,024 addresses a system for process data association using LaPlace Everett interpolation.

U.S. Pat. No. 6,051,209 covers a method of evaluating the effects of administering external stimuli or a treatment on the brain using positron emission tomography.

Section 1.2.2.4 cites two web pages. Section 4.2.4 also quotes the first of these two web pages. The two web pages are:

Institute for Systems Biology, What is Systems Biology, URL http://www.systemsbiology.org/workwhat.html, Viewed Apr. 10, 2001; and Institute for Systems Biology, History of Concepts Leading to the Institute, URL http://www.systemsbiology.org/workhist.html, Viewed Apr. 10, 2001.

Section 1.2.2.4 also cites the following article:

T. Ideker, V. Thorsson, J. A. Ranish, R. Christmas, J. Buhler, J. K. King, R. Bumgamer, D. R. Goodlett, R. Aebersold, L Hood, *Science*, 292, 929–934, 2001.

Data for the hormone data example in Section 4.9 were described and presented in the following citations:

Padmanabhan, V., McFadden, K., Mauger, D. T., Karsch, F. J., and Midgley, A. R. (1997). Neuroendocrine control of follicle-stimulating hormone (FSH) secretion. 1. Direct evidence for separate episodic and basal components of FSH secretion. *Endocrinology* 138, 424–432, and;

Midgley, A. R., McFadden, K., Ghazzi, M., Karsch, F. J., Brown, M. R., Mauger, D. T., and Padmanabhan, V. (1997). Nonclassical secretory dynamics of LH revealed by hypothalamo-hypophyseal portal sampling of sheep. *Endocrine* 6, 133–143.

BRIEF SUMMARY OF THE INVENTION

This invention is a method or system to construct at least one profile representing how the actions of an object of investigation are coordinated, the profile(s) being based on computed measures of longitudinal association or temporal contingency that quantify patterns of interaction in repeated measures or time series data that include two or more variables for one individual. Such profiles are called action coordination profiles (ACPs).

ACPs can provide quantitative descriptions of how individual complex systems may control and regulate themselves, of how two or more individual systems may interact, of how complex systems may be controlled or affected by their environments including treatments, and of how individual systems may control or affect their environments.

In practice, ACPs are limited to selected variables and episodes of action for particular objects of investigation. This is illustrated by the examples in Section 4.9. One example involves certain pituitary and reproductive hormones measured every 5 minutes for up to about 12 hours for individual ewes. Another example involves variables considered to affect the Gross Domestic Product of the United States economy using quarterly data for about 42 years.

The title of parent application Ser. No. 09/470,956 is "Computational Method and System to Perform Empirical Induction." Empirical induction involves procedures to draw generalized conclusions and make predictions from data. More specifically, this invention and its parent involve computational procedures to provide high quality generalized conclusions and predictions as high quality is defined in Section 1.2 of the parent application.

The key innovative concept for this invention and its parent comprises a computational method and system specifically designed to process repeated measures and time series data to measure interactions between and among variables for objects of investigation that are individuals. The parent application describes the Method for the Quantitative Analysis of Longitudinal Associations (MQALA).

MQALA and ACPs include an extensive set of computational tools and analytic options that users can select and apply to address many types of problem encountered in scientific investigations and practical affairs. All these tools and analytic options are based on a core set of computational methods or systems.

This invention and its parent are distinct from and often complementary to the statistical method. As such, this invention facilitates scientific investigations of individuals both as individuals and as members of collective entities. For example, these inventions often can be used to facilitate both the individualization of medical care and the conduct of group clinical trials for treatments used to control or manage chronic disorders.

Since ACPs are a direct extension and distinct improvement on the parent application, much material in the parent application also applies to ACPs. Many terms used in this application are defined in Section 2.9 of the parent application.

The following subsections provide a brief summary of the structure of ACPs as well as how they are constructed, functions of ACPs, and how ACPs address limitations of the statistical method as well as the five specific previously identified problems involved in the prior art.

2.1. Structure of ACPs

An ACP can be characterized as a set of computed measure values, the set having two dimensions. One dimension represents independent events and a second dimension represents dependent events. Each column or row for the dimension representing independent events corresponds to one of two or more variables or sets of variables or the results of applying certain features used to define independent events. Each column or row for the dimension representing dependent events corresponds to one of two or more variables or sets of variables or the results of applying certain features used to define dependent events.

Table 1 illustrates the general structure of an ACP with 10 variables and only one column or row for each variable. The same variables are used for both dimensions. Rows represent the variables functioning as independent variables (IVs) to define independent events. Columns represent the variables functioning as dependent variables (DVs) to define dependent events. Cells are formed at intersections of rows and columns.

Table 1 uses the symbols "o" and "*" to represent scores or measure values in general. Each cell of Table 1 that contains an "*" indicates that the score or measure value was obtained when the variable labeling a row was functioning to define independent events. Each cell of Table 1 that contains an "o" indicates that the score or measure value was obtained when the variable labeling a column was functioning to define dependent events. There are no measure values for cells on the concordant diagonal, which are represented with the symbol "-". Additional columns and rows would be used to represent Boolean events defined on two or more variables, to represent transition events, or to represent additional ways of defining independent or dependent events.

TABLE 1

Structure of an ACP with ACP with 10 variables.

| | | | | DVs | | | | | | |
|---|---|---|---|---|---|---|---|---|---|---|
| | | 1 | 2 | 3 | 4 | 5 | 6 | 7 | 8 | 9 | 10 |
| IVs | 1 | — | 0 | 0 | 0 | 0 | 0 | 0 | 0 | 0 | 0 |
| | 2 | * | — | 0 | 0 | 0 | 0 | 0 | 0 | 0 | 0 |
| | 3 | * | * | — | 0 | 0 | 0 | 0 | 0 | 0 | 0 |
| | 4 | * | * | * | — | 0 | 0 | 0 | 0 | 0 | 0 |
| | 5 | * | * | * | * | — | 0 | 0 | 0 | 0 | 0 |
| | 6 | * | * | * | * | * | — | 0 | 0 | 0 | 0 |
| | 7 | * | * | * | * | * | * | — | 0 | 0 | 0 |
| | 8 | * | * | * | * | * | * | * | — | 0 | 0 |
| | 9 | * | * | * | * | * | * | * | * | — | 0 |
| | 10 | * | * | * | * | * | * | * | * | * | — |

Each cell in Table 1 that is identified by an "*" or an "o" represents a particular interaction. Particular interactions also can have dimensions. Dimensions for particular interactions represent analysis parameters such as level of the independent variable, level of the dependent variable, delay, persistence, episode length and episode criteria for the independent variable, and episode length and episode criteria for the dependent variable.

The term "dimension" is being used in two contexts. In the context of ACPs, "dimension" refers to variables functioning to define either independent or dependent events. In the context of particular interactions that are represented by cells, "dimension" refers to analysis parameters that may or may not have multiple levels.

The computed measure values in ACPs generally are either longitudinal association scores or values of measures derived from longitudinal association scores. Section 4.4 identifies examples of measures that can be used to construct ACPs. Typically, the magnitude of each score or measure value in ACPs quantifies either the amount of evidence for a longitudinal association or the strength of that association. The signs of longitudinal association scores indicate positive or negative associations. Positive scores indicate that dependent events are more apt to occur in the presence of independent events than in the absence of independent events. Negative scores indicate that dependent events are less apt to occur in the presence of independent events than in the absence of independent events. Zero scores or measure values indicate no evidence for longitudinal associations or temporal contingencies.

Each of the variables used to define independent and dependent events for ACPs would need to be measured or assessed repeatedly for an individual on two or more occasions. In addition, each variable should have the potential to vary—fluctuate in level or recur over time—for the object of investigation represented by the ACP. Variables could be transformed mathematically before computing scores or measure values in ACPs.

ACPs can be portrayed as tables, figures, graphs, and displays. It is recommended that columns and rows in ACPs for particular types of investigation be presented in standardized orders to facilitate comparisons and analyses of profiles for different individuals or for different episodes of action.

Unless otherwise specified, the same variables and features would be used in the same way to define both independent and dependent events for ACPs. This means that people who construct ACPs generally need not identify variables or events as independent or dependent. Furthermore, this is in accord with how complex systems often function. A given event may function as a dependent event with respect to some other events and the same given event may function as an independent event with respect to still other events.

In some cases, events may function in feedback loops to affect more events of the same type. For example, neurotransmitters can have both pre- and post-synaptic receptors so that release of a transmitter can help propagate a signal and feed back to affect release of additional transmitter.

Features of MQALA can be used alone or together with experimental procedures to help distinguish causal from non-causal associations. Some portions of ACPs could remain blank if, for example, investigators determine that it would not be meaningful to consider variables that were under control in experimental investigations to function as dependent variables.

Typically, various analysis parameters would be used to obtain the measure values in ACPs. Level of independent variable and level of dependent variable are required analysis parameters when the variables are dimensional (when a series of values for a variable has more than two different values) and the user of MQALA decides to examine more than two levels.

Another analysis parameter, delay, would be a primary analysis parameter when ACPs are used to investigate the temporal criterion of causal and other predictive relationships (Section 4.8.9). Delay is defined on variables functioning as independent variables. Users of ACPs could specify one or more particular values of delay or a range of values. One ACP or portion of an ACP would be computed for each particular value of delay. In addition or alternatively, one ACP could summarize scores across a range of values of delay.

Additional analysis parameters for interactions that are described in the parent patent application include episode length and episode criterion for independent and dependent variables as well as persistence defined on variables functioning as IVs. Users can define additional analysis parameters. Typically, the same scoring options would be selected for each IV and for each DV that are used in particular ACPs.

Typically, scores actually shown in ACPs would be summary scores. Information about the location of each summary longitudinal association score or derivative measure in an array identifies the conditions that yielded the summary measure. These conditions are defined in terms of features such as analysis parameter levels and Boolean events. Users would be able to drill down from scores shown in summary ACPs to examine scores as functions of analysis parameter levels and in terms of Boolean events.

2.2. Functions of ACPs

ACPs are a way of displaying particular types of quantitative information so that it can be used to discover and describe patterns of longitudinal association or temporal contingency between and among variables and events. Use of ACPs to discover and describe patterns in a systematic, comprehensive, and detailed manner will advance the objectives of scientific investigation, the conduct of practical affairs, and decision-making.

The author has coined various terms to describe ACPs and the methodology upon which they are based. These terms emphasize different ways in which the technology is unique and of value.

MQALA can be viewed as a contribution to "temporal contingency analysis." The contingencies (associations) involve independent and dependent events defined in multidimensional spaces formed primarily by applying analysis parameters and Boolean operators to transformations of repeated measures data including time series.

Independent and dependent events can be defined in great detail. Analysis parameters account for things such as levels of independent (predictor) and dependent (predicted) variables. Optional analysis parameters account for things such as episodes of events. Here is an example of an independent event defined using such parameters and a temporal resolution of one day. Did or did not a given patient meet the criterion on each of a series of days of taking 100 mg or more of a given drug (Drug 1) on 5 out of 7 consecutive days? Additional optional analysis parameters can be used to define temporal aspects (delays and persistencies) of relations between events.

Boolean operators can be applied to events defined with analysis parameters to define additional events called Boolean events that are based on two or more independent or two or more dependent variables. For example, a Boolean independent event could consist of meeting the criterion defined for Drug 1 in the preceding paragraph AND the criterion of taking Drug 2 at a dose of 50 mg or more on 4 out of 6 consecutive days. The presence of such a Boolean AND independent event may be sufficient, for example, to increase the presence of a particular type of dependent event such as the level of a liver enzyme being above the upper limit of normal.

MQALA analyzes such contingencies between independent and dependent events. Many thousands of different events and types of events can be analyzed simultaneously in particular investigations to identify the levels of analysis parameters and the Boolean events that yield the most evidence for associations or interactions.

The "temporal" in "temporal contingency analysis" indicates that MQALA and any particular ACP quantifies and describes the directions and amount of evidence for contingencies (associations or interactions) between and among events as these contingencies are evident in data that are about the individual and are collected over time from the individual. MQALA also quantifies the strength of associations, contingencies, or interactions. MQALA's capability to analyze temporal contingencies derives from the fact that it is applied to longitudinal, repeated measures, or time-series data as relatively distinct from cross-sectional data.

ACPs also can be described with coined terms such as "action coordination fingerprints," "movement coordination fingerprints," "behavior coordination fingerprints," and "interaction fingerprints." The term "fingerprints" in such descriptions focuses attention on the fact that ACPs can describe that that is characteristic of individuals that may be unique or different from other individuals. In addition, ACPs can be used to describe that that is characteristic of episodes of coordinated action, movement, or behavior for individuals. For example, episodes of coordinated locomotion of horses have been characterized as walk, cantor, trot, and gallop.

The term "fingerprints" in its conventional use refers to the form or structure of skin on the fingers. In contrast, ACPs fingerprint something that is more abstract and conceptual—namely the way actions interact. Interactions indicate coordination. ACPs can fingerprint how individuals function, control, and sustain themselves as well as interact with each other and their environments.

2.3. How do ACPs Help Address Limitations of the Statistical Method?

Section 1.2 of this application describes related art in the context of creating, verifying, and refining mathematical models that represent objects in the world. More specifically, the referenced section presents certain limitations and problems related to using the statistical method for this purpose. This section and its subsections describe how MQALA and ACPs help address these limitations and problems.

Both MQALA, which now includes ACPs, and the statistical method are distinct and often complementary computational methods of empirical induction. Computational methods and systems of empirical induction are used to draw generalized conclusions and make predictions from data.

Although both MQALA and the statistical method are computational methods of empirical induction, they are distinct in other key respects. These distinctions include the type of data (evidence) that the two methods are best suited to analyze, the objectives of analyses, the computational procedures themselves, and the type of entities about which conclusions are drawn and predictions are made.

2.3.1. MQALA and the Statistical Method Are Best Suited to Analyze Distinct Types of Data (Evidence)

MQALA analyzes repeated measures or time series data for particular individuals. MQALA requires data for at least two variables or types of events. At least one variable must function as an independent variable and at least one variable must function as a dependent variable. Both independent and dependent variables must vary within individuals in order to obtain nonzero longitudinal association or benefit/harm scores.

In contrast to MQALA, the statistical method is best suited to analyze cross-sectional data for groups of individuals. Inferential statistical procedures (as contrasted to descriptive statistical procedures) also generally require data for independent and dependent variables from groups with two or more individuals per group.

Thus, from what has been said about the type of data best suited for analysis by MQALA and the statistical method, the two methods generally rely on different types of evidence for relationships between and among variables. MQALA relies on longitudinal associations (temporal contingencies) between and among variables within individuals. In contrast, the statistical method is best suited to analyze cross-sectional associations—differences between and among individuals or groups of individuals.

The statistical method is best suited for analyses involving groups of different individuals at one or only a few times. In contrast, MQALA and ACPs are best suited for analyses involving one individual at many different times.

2.3.2. MQALA and the Statistical Method Have Distinct Objectives

Objectives of analyses conducted with MQALA are to quantify, discover, analyze and describe longitudinal associations (temporal contingencies) between and among variables within individuals. MQALA provides generalized conclusions about longitudinal associations between and among variables for individuals. Such conclusions are generalized over repeated measurements. MQALA does this with a variety of scores including scores presented in the form of ACPs.

MQALA also supports predictions. These predictions are about how individuals will function or respond in the future. Predictions are based on the assumption that past experience can be used to help predict the future.

MQALA supports predictions in at least two related ways. First, generalized conclusions about how an individual has functioned or responded to date can be used to make predictions about how that individual will respond or function in the future. For example, assume that a benefit/harm score based on many repeated measurements of drug dose and blood pressure for a particular patient over the course of the last year indicates that the drug had a substantial beneficial effect for that patient. This score would support the prediction that the same drug would continue to have the same beneficial effect for the same patient over the course of the next month.

MQALA also supports predictions with a feature called predictive indices. Predictive indices are one way to use information from two or more predictors (IVs) or sets of predictors used to define Boolean events to make predictions about a predicted variable (DV). Predictive indices are computed directly from information used to compute particular longitudinal association scores.

MQALA supports direct predictions. That is, the predictions are for the same individual that the data are about. Furthermore, the predictions are for the same variables analyzed with the same analytic options.

MQALA does not directly support inferences from one individual or group of individuals to another. However, MQALA provides scores and other measures that can be analyzed statistically to make such inferences when the scores or measures are available for two or more individuals. This illustrates the complementarity of MQALA and the statistical method.

MQALA is a powerful new set of computational tools for drawing conclusions and making predictions about individuals by providing quantitative descriptions of experience that has been recorded as repeated measures data.

In contrast to MQALA, the statistical method is best suited to describe characteristics of groups and to quantify, discover, analyze and describe cross-sectional associations between and among variables for groups of individuals. In addition, the statistical method includes procedures for using group descriptions to make statistical inferences from samples of individuals to populations of individuals.

Descriptive statistics are best suited to describe groups of individuals. The application of such group descriptions to individuals is indirect. Similarly, statistical inferences generally are for groups rather than for individuals.

Conventional parallel group clinical trials are conducted primarily for the benefit of groups of patients that may be candidates for treatment in the future. This fact often raises ethical questions concerning the patients who actually participate in conventional group clinical trials.

2.3.3. MQALA and the Statistical Method Use Distinct Computational Procedures The computational procedures for MQALA and the statistical method differ in several important respects. Unlike the statistical method, MQALA must convert any dimensional series for independent and dependent variables into sets of dichotomous series. All analysis parameters and Boolean events are defined on such dichotomous series. Dichotomous series for independent variables and dichotomous series for dependent variables a re cross-classified to yield 2×2 tables. This procedure can easily yield thousands of 2×2 tables for any particular individual.

MQALA continues by computing standardized longitudinal association or benefit/harm scores for each of these 2×2 tables. These scores are standardized with respect to all scores that are possible given the marginal frequencies of observed 2×2 tables. Standardization allows the scores to be summarized and compared. In addition, standardization makes it reasonable to compute overall benefit/harm scores across many dependent variables for particular individuals. Overall benefit/harm scores can be computed with or without differential weights.

Longitudinal association scores, benefit/harm scores, and overall benefit/harm scores—one score from each of two or more individuals—can be analyzed statistically. This illustrates the complementarity of MQALA and the statistical method.

2.3.4. MQALA and the Statistical Method Are Best Suited for Distinct Types of Entities A key distinction between MQALA and the statistical method involves the type of entities for which the methods are best suited to draw conclusions and make predictions. MQALA draws conclusions and makes predictions about individuals. For MQALA, individuals include populations investigated as wholes. In contrast, the statistical method is best suited to draw generalized conclusions and support predictions about groups and populations of individuals.

Both MQALA and the statistical method are tools for the conduct of objective scientific investigations. Systematic scientific knowledge generally is considered to involve generalized conclusions rather than particulars.

MQALA can be used to make generalized conclusions about individuals. Such conclusions are generalized over time within individuals where time is represented by repeated measurements.

In contrast to MQALA, the statistical method is best suited to draw generalized conclusions about groups. Descriptive statistics generalize across the individuals that comprise groups. Statistical inferences generally are based on group comparisons and sample data. Such results apply only indirectly to individuals.

2.4. MQALA Helps Address Problems Described in Section 1.2.2.

The following subsections provide additional information about each of the problem areas described in Section 1.2.2 with a focus on the ACP component of MQALA.

2.4.1. ACPs Help Address Problems Involving Individuality

Since an ACP is computed from data about an individual, the ACP applies most directly to the individual that the data are about. Section 2.6 of the parent patent application discusses differences between direct, indirect, and doubly indirect predictions together with some advantages of using direct predictions for individuals.

Differences between direct, indirect, and doubly indirect predictions can be illustrated in the context of conventional parallel group clinical trials. Although such trials provide valuable information about both groups and group members, the application of results from such trials to individuals is doubly indirect. One source of indirectness involves the extent to which samples represent populations. A second source of indirectness involves the extent to which particular individuals are typical of average population members.

The parent application also explains how measures of longitudinal association, such as those used in ACPs, can be reliable and valid measures of longitudinal association for individuals. In brief, applying experimental procedures within individuals can enhance validity. Collecting and analyzing data from many repeated measurements can increase reliability.

ACPs can be computed to describe how the parts, variables, and manifestations of unique individuals interact. For example, the US economy is a relatively unique individual. It generally is not feasible to investigate unique individuals by sampling populations and making inferences from the samples. For such reasons, MQALA is better suited than the statistical method to investigate individuals that are unique.

ACPs also can be computed for individuals that may be different—not typical—of average individuals. For example, patients with high blood pressure can differ with respect to concurrent disorders, concomitant treatments, gender, race, age and other factors. Conventional strategies for investigating treatments favor homogenous groups of substantial size. It can be difficult to recruit samples of substantial size when many factors differentiate patients. The number of populations that need to be investigated also increases with the number of factors that differentiate patients. The number of populations that need to be investigated and the number of individuals available in each population clearly limit the strategy of investigating homogeneous groups. MQALA, including ACPs, address such problems by providing unique functionality to help enable scientific investigations of individuals.

Scientific investigations, whether of groups or of individuals, have well known advantages such as providing objective and repeatable results. Some unique advantages of conducting scientific investigations of individuals can be considered from the practical and epistemological perspectives.

From a practical perspective, therapy often needs to be individualized because patients differ from one another in their responses and preferences. MQALA appears to be the missing key for providing individualized or personalized health care that is for people with chronic health concerns and based on objective scientific procedures for drawing generalized conclusions and making predictions from data. Chronic disorders and their treatments often are investigated best with repeated measures and time series data.

From an epistemological perspective, MQALA can be used to help discover how individual differences affect susceptibility to disease and response to therapy. Differences relevant to both include genetic differences.

Another reason why MQALA is an important analytic tool is that it helps enable scientific investigations of how individuals interact with their physical and social environments. The uniqueness, richness, and continuity of such interactions appear to be the essence of individual identity.

2.4.2. ACPs Help Address Problems Involving Complexity

MQALA, which now includes ACPs, can help address complexity by simultaneously measuring how many variables interact for objects that are individuals. The variables can be internal or external to the object. The interactions can involve variables both within and across levels in measurement hierarchies. The variables can act in different combinations. Any interactions can be positive or negative.

ACPs are a new way to image complexity as it becomes evident in how individuals function, respond, and act as agents. Images of complexity based on ACPs can help users visualize complexity. Visualizing complexity can help make it understandable.

Images of functional and response complexity should be distinguished from images of structural complexity. Brain scans obtained by Computerized Axial Tomography illustrate structural complexity. In contrast, an ACP of an individual's brain could show how every region of the brain interacts with every other region of the brain. Such an ACP, which would illustrate functional and response complexity, would be easier to understand if it were obtained under a given set of test conditions. ACPs that image functional complexity of individual brains can be computed from a series of functional brain images (Section 4.2.7.2).

ACP images of functional and response complexity can be very extensive. ACPs can have a virtually unlimited number of rows and columns for each dimension. For example, an image showing functional interconnectivity of brain regions could have one row and column for each of the corresponding pixels in the series of functional magnetic resonance images from which it is computed. Additional levels could be added for Boolean events.

The ways in which MQALA addresses functional complexity can be viewed from other perspectives.

One reason why MQALA, including ACPs, is a significant advance in human history is that although human judgment seems to rely heavily on longitudinal associations and temporal contingencies, prior art computational methods and systems for analyzing longitudinal associations have limited functionality. In contrast, computational methods and systems for analyzing cross-sectional associations are well developed.

The importance of longitudinal associations and temporal contingencies in human judgment can be illustrated in the context of clinicians judging the effects of drugs on patient health. Clinicians often judge how individual patients respond to drug challenge, de-challenge, re-challenge, and other changes of dose. Clinicians often plan continued treatment of individual patients in accord with such judgments. Learning from such judgments can be contrasted with learning from conventional group clinical trials. Sections 2.8.2 and 4.2.2.2 of the parent patent application describe many advantages of using MQALA, a computational method and system that can supplement human judgment, to help individualize patient care.

Longitudinal associations and temporal contingencies also appear to play important roles in the workings of nature. The capacity of brains to learn appears to have evolved in a way that allows animals (including people) to learn from temporal contingencies involving stimuli, responses, and reinforcers. Only recently have humans begun to learn by applying the statistical method. Much of human associative learning also appears to involve temporal contingencies and an extension of learning capabilities from emotional and motor responses to more abstract and conceptual entities. Sections 4.2.5 and 4.2.6 of the parent patent application includes a discussion of how classical conditioning, instrumental conditioning, and paired associate learning can be analyzed with MQALA and of how this knowledge can be used to create machines and artificial systems that learn.

MQALA is an important advance in scientific methodology and for the application of technology to achieve human objectives because ACPs can help users visualize functional and response complexity; facilitate the creation of mathematical models of how complex systems function, respond, and act; as well as the creation of artificial systems that learn.

2.4.3. ACPs Help Address Problems Involving Nonlinearity

The computational procedures upon which ACPs are based address nonlinearity in at least two primary ways.

First, MQALA converts dimensional series into sets of dichotomous series using integrated scales as described in Section 4.1.2 and illustrated in Tables 6 and 7 of the parent patent application. The values of measures portrayed in ACPs are computed from cross-classifications of independent and dependent events as defined on such dichotomous series as illustrated for longitudinal association scores in Section 4.1.1 of the parent application. As such, the computational procedures do not assume that effects of independent variables or events on dependent variables or events are proportional to independent variable levels.

Second, MQALA can use Boolean independent events and Boolean dependent events to help determine if particular combinations of events are associated more with other events than with the same variables considered individually. This use of Boolean events, described in Section 4.1.11 and illustrated in Table 17 of the parent application, addresses the problem of non-additivity as described in Section 1.2.2.3 of this application.

2.4.4. ACPs Help Address Problems Involving Comprehensive Investigations

Section 1.2.1.2.1.2 and its subsections in the parent application describe a number of problems involving comprehensiveness and detail in the context of evaluating treatments for health disorders. Section 2.7.1.2.1.2 and its subsections in the parent application describe how MQALA helps address these problems. Furthermore, Section 4.2.1.1 of the parent application includes information about how MQALA addresses problems involving the emergence of system properties and unique entities—problems that are included in Section 1.2.1 also of the parent application. ACPs further address the problems involving comprehensiveness as described is Section 1.2.2.4 of this application because of the capability of ACPs to provide quantitative displays of large numbers of interactions simultaneously. Measurement of the interactions for an individual effectively converts the interactions into a multidimensional object that can be visualized, graphed, and subjected to established quantitative methods such as those of morphometrics.

MQALA, including ACPs, is an advance in data processing that helps make systems biology and discovery science possible. Furthermore, MQALA can be applied to many types of complex system in addition to biological systems. This flexibility of application derives from the fact that MQALA can be applied to data for various types of entity much as the statistical method can be applied to data for various types of entity. However and again, a fundamental distinction between the two methods is that MQALA is specifically designed for application to individual entities while the statistical method is best suited for collective entities.

2.4.5. ACPs Help Address Problems Involving Detailed Investigations

There are at least two ways that ACPs and MQALA can help address the need for detailed investigations. First, ACPs can address interactions between and among a virtually unlimited number of variables. This can, for example, help users avoid problems that can result when investigators lump many health variables into a single health measure.

Second, each score in an ACP typically would be a score that summarizes a multidimensional array of scores. The dimensions of arrays correspond to analysis parameters such as IV level, DV level, episode length, episode criterion, and persistence. Users of ACPs and MQALA would be able to drill down into these arrays to examine in great detail the interactions shown in ACPs.

2.4.6. Addressing the Need to Investigate All Five Types of Problem as a Set MQALA is an integrated set of data processing tools built around core computational measurement methods and providing users with many options about how to proceed. These core computational methods measure longitudinal associations between and among variables and events for individual entities that are complex systems. As such, MQALA addresses all of the five problem areas—individuality, complexity, nonlinearity, comprehensiveness, and detail—as a set.

In practice, all things cannot be investigated at once. Investigators are limited by the number of variables that can be measured simultaneously, by the temporal resolution of data, and by the number of repeated measures that can be included in particular investigations. Computer resources for analyzing data are limited. This is one reason why users of MQALA and ACPs will be limited in the number of analysis parameters, analysis parameter levels, and Boolean events that can be included in particular investigations.

Despite such limitations, MQALA facilitates investigations that are both more comprehensive and detailed than investigations conducted with conventional data processing procedures. As such, MQALA can help make better use of data that can be collected now. In addition, several uses of ACPs are designed to help address the research strategy dynamic involving detailed and comprehensive investigations. As examples, Section 4.8.8 describes how ACPs can be used to measure interactions involving different types of action. Section 4.8.11 describes use of ACPs to investigate nested systems. Section 4.8.12 describes use of ACPs to distinguish episodes of action. Section 4.8.4 describes how ACPs can be used to fingerprint individuals, fingerprints that can be used to develop classifications of individuals into groups that are more homogeneous with respect to how they function and interact with their environments. Such uses provide tools both for partitioning the subject matter of science and for examining how the parts interact to form complex systems.

MQALA is based on a tenet that is central to science: If you want to investigate something scientifically, measure it! MQALA measures the interactions between and among variables and events that help reveal how complex individual systems of many types function, regulate, and sustain themselves as well as how they respond to and act upon their environments.

The above objects and other objects, features, and advantages of the present invention are readily apparent from the following detailed description of the best mode for carrying out the invention when taken in connection with the accompanying drawings.

BRIEF DESCRIPTION OF THE SEVERAL VIEWS OF THE DRAWING

FIGS. 2 and 3 are described in Section 4.9.

DETAILED DESCRIPTION OF THE INVENTION

Figure 1:
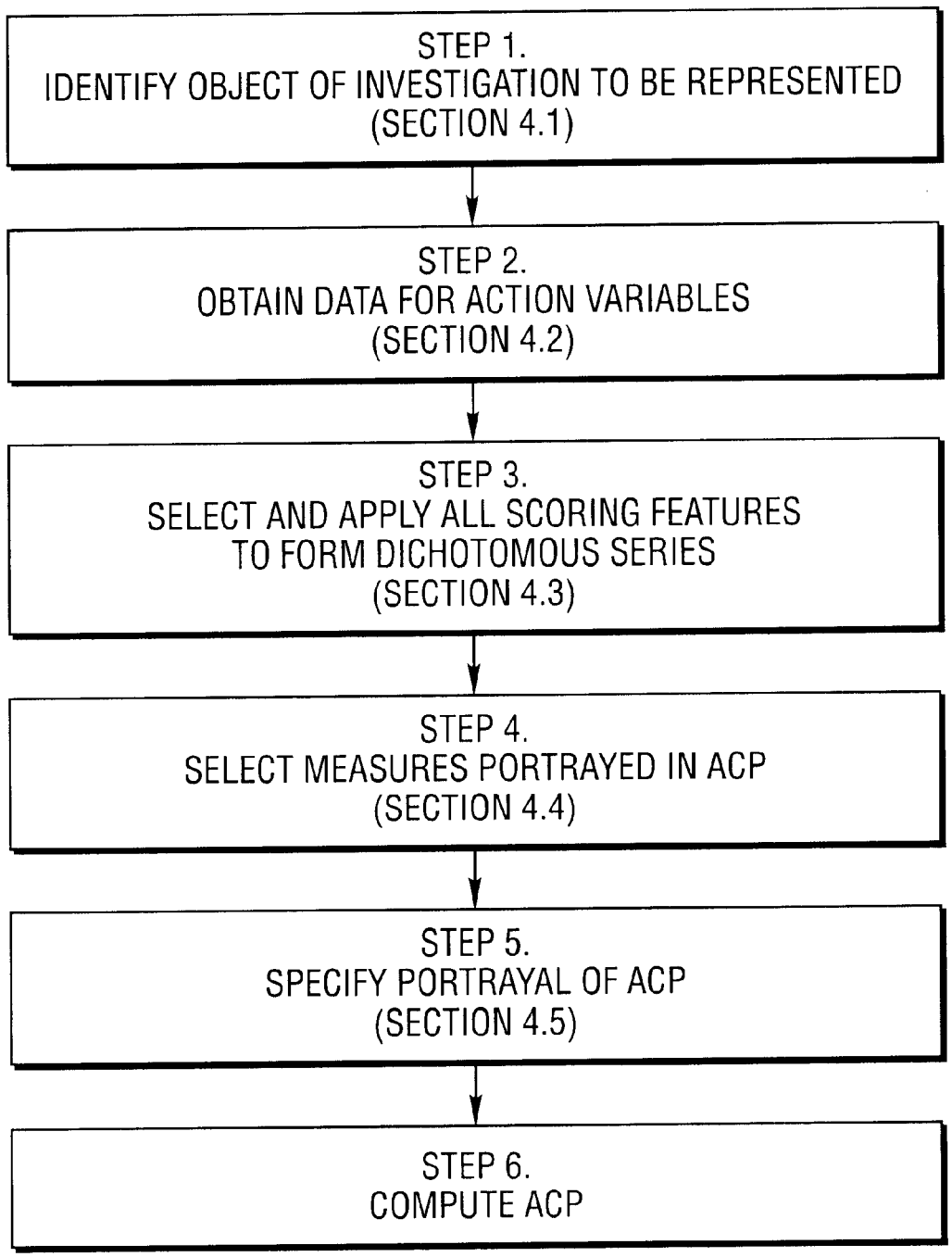
FIG. 1 illustrates steps to construct ACPs.

This invention is a platform data processing technology that applies to various types of objects and actions, has various computational features, and many uses.

This section provides a detailed description of ACPs. The first major subsection illustrates types of objects that can be represented by ACPs. Objects are distinguished from their environments.

The next major subsection illustrates types of action that can be manifested by and upon various objects of investigation. Several measurement technologies yield data that are particularly well suited for processing to yield ACPs. Major components of established sciences and disciplines can be investigated with ACPs.

Subsequent major subsections identify various features that can be used to compute ACPs and types of scores and measures that can be portrayed by ACPs. These features, scores, and measures will be presented primarily by reference to specific sections of the parent patent application. ACPs themselves can be portrayed in various ways that will be illustrated in a major subsection.

Additional major subsections illustrate uses of ACPs, cover databases that include ACPs, and statistical analyses of two or more ACPs. The final major subsection presents several examples of ACPs.

4.1. Objects of Investigation and Their Environments

ACPs can be used to investigate objects that are complex systems of many types. Systems are considered to be complex when they have many parts, variables, or manifestations that can interact. A system also is considered to be complex when many things in its environment can act upon it. Here are some examples of complex systems that can be investigated with ACPs. These examples are not exhaustive or mutually exclusive.

4.1.1. Organisms Including Persons

An organism has been defined as a complex structure of interdependent and subordinate elements whose relations and properties are largely determined by their function in the whole. Organisms carry on the activities of life. Organisms are considered to include persons.

4.1.2. Portions of Organisms

Portions of organisms include cells, tissues, organs, systems, biochemical pathways, and biopathways. Such portions of organisms have differentiated structures or functions.

4.1.3. Economies and Investment Markets

Economies and investment markets are complex systems that can be objects of investigation with MQALA including ACPs. Such investigations are particularly feasible because there are vast amounts of readily available time series data for these objects.

Scientific investigations of how economies and investment markets function can be particularly valuable because of the way improvements in economic policy can affect society and the way accurate predictions can affect investment profits.

4.1.4. Machines, Processes, and Other Man Made Systems

People make machines, processes, and other complex systems that can be objects of ACPs. This can be illustrated with refinery processes that can be monitored in terms of inputs and outputs for product streams. Such monitoring can produce time series data that can be analyzed with MQALA. Resulting measures of interaction can be used to identify how inputs can be controlled to help optimize refinery processes.

Other examples of man made systems include healthcare, banking, and software systems whose behavior can be monitored with time series data.

4.1.5. Systems Consisting of Two or More Individuals

ACPs can be used to investigate reciprocal interactions of objects involving two or more individuals that may interact to form compound objects. This can be illustrated with episodes of dance in which the object is a pair of dancers and the actions are the movements of both dancers (Section 4.2.1). ACPs can be used to describe the nature and extent to which movements of dancers are coordinated.

Individuals forming compound objects need not be of the same type. For example, a horse and a rider or a man and a machine form compound objects.

The same approach could be extended to compound objects with more than two members such as teams. Numbers of variables and numbers of Boolean events that could interact would tend to increase rapidly with the number of individuals in compound objects.

4.1.6. Populations Investigated as Wholes

Section 2.6 of the parent application describes how MQALA can be applied to objects that are populations investigated as wholes. Investigating populations as wholes is distinct from making inferences about populations from samples of populations' individuals.

The section just referenced illustrates the research strategy of investigating populations as wholes in the context of epidemiology. This strategy can, for example, use environmental variables such as measures of air pollution that are considered to affect whole populations together with population variables such as rates of death or hospital admission. ACPs for populations considered as wholes could be based for many variables considered to affect populations as wholes and various population rates and proportions.

4.1.7. Nested Systems

Complex systems often can be investigated as series of individuals with differing degrees of inclusiveness. Inclusiveness involves physical, functional, and conceptual boundaries identified or set by investigators to help distinguish that which is within systems from that which is part of systems' environments. Thus, for example, investigators of biological systems often distinguish endogenous from exogenous substances.

Here is an example of a nested system in the context of investigations of living things in which each successive individual can be considered to be nested within the next level: cell, organ, organism, and social system. Another example in the context of biological systems is neuron, brain, and organism.

Here is an example of a different type of problem that can be addressed using nested systems: attempting to predict the price of an individual company's stock. Starting from the least inclusive level of investigation for this particular example, the company's stock price can be investigated in terms of its own periodic measures of business performance. Then the stock's price could be investigated in terms of various stock sectors including the sector of which the stock of interest is a member. Then the price of a broad range of stocks across many sectors could be investigated in terms of other potential investments in a particular country's economy such as bonds, real estate, commodities, and collectibles. Finally the performance of a particular country could be investigated in the context of periodic measures of how other countries perform.

Activity at each level of a nested system can be expected to have effects on the activity of included component individuals. Thus, for example, the performance of the economy of the United States in the world economy could be expected to have effects on stock prices for individual companies.

Similarly, individual companies' performances could be expected to have effects as agents on more inclusive levels in nested systems. Thus, for example, the performance of a major United States company could be expected to have some impact on the performance of the economy of the United States in the environment of the world economy.

ACPs can be used to investigate reciprocal interactions between individuals and their environments when the systems are defined to have the different degrees of inclusiveness that are characteristic of nested systems. This can be done when measures of action for one component of a nested system become variables for computing ACPs for other more or less inclusive components of the nested system.

Sections 4.1.17 and 4.4.3.8 of the parent application describe predictive indices, which are another component of MQALA. Predictive indices can be an efficient and operational way to summarize the effects of many independent variables or predictors so that many types of action can be summarized in one variable that can in turn be used for computing ACPs for nested systems.

Here is an example of how predictive indices could be used to investigate a system consisting of a neuron nested in a relatively simple brain. Suppose that it is feasible to obtain time series data on variables that may influence the rate at which a neuron fires together with data for the neuron's firing rate. The predictive index feature of MQALA could be used to summarize the effects of two or more variables that affect firing rate. Then the predictive index could be included as a variable in an ACP that also includes variables describing action of the brain of which the neuron is a part. Such strategies could be used to help elucidate reciprocal interactions involving nested systems.

4.1.8. Additional Types of Systems

ACPs can be computed for systems that can be investigated with time series data for variables that fluctuate in level or recur over time. Examples include social systems, ecosystems, and weather systems.

4.2. Actions

Various types of objects that can be represented by ACPs manifest actions of many types. The following subsections illustrate various types of action that can be measured to yield data that are processed to construct ACPs. Resulting ACPs go beyond levels of variables from which they are computed to reveal how variables interact to form functioning systems. Procedures for obtaining data that are to be processed to construct ACPs can be specified in protocols.

Measurement technologies, here considered as they measure various types of action, are improving rapidly, often in several ways simultaneously. Here are examples of different ways in which measurement technologies are improving.

New measurement technologies are measuring things that were never measured before. For example, modem imaging technologies can measure brain activity such as areas of the brain that are activated while performing mental arithmetic. Rating scales are being developed to operationalize concepts at high levels of measurement hierarchies, concepts such as health-related quality of life.

Measurement technologies are becoming more sensitive. For example, they can detect and measure concentrations of parts per billion or less.

Some measurement technologies can measure thousands of variables simultaneously. Microarrays that are used in biotechnology can measure thousands of variables on one chip.

Some measurement technologies are achieving high temporal resolution. Temporal resolution refers to the number of repeated measurements per unit time. Some processes can be measured repeatedly to yield time series data with many measurements per second.

Measurement devices are being miniaturized. MicroElectroMechanical Systems (MEMS) for sensing flow, pressure, and chemicals are being developed that can operate from within the human body.

Measurement devices are being Internet enabled. For example, Internet enabled medical monitoring devices can report health variables from almost anywhere.

Most improvements in measurement technologies, inventive as they are, are conventional in an important way. That is, most conventional measurement technologies measure variables one by one as distinct from how the variables interact to form complex functioning systems. In contrast, this invention measures how variables interact to form complex functioning systems.

This invention is a computational method and system. The input for this invention can comprise much output from conventional measurement technologies. The output from this invention comprises quantitative descriptions of how complex individual systems function. As such, this invention increases the value of many conventional measurement technologies.

Here are some examples of types of action that can be measured and serve as input for this invention. The following types of action are not mutually exclusive or exhaustive. The following subsections include information about how ACPs for various types of action can be useful.

4.2.1. Movement

ACPs were inspired by the task of analyzing data collected by motion capture technology. One such technology that can be applied to humans uses 36 reflective markers on various parts of the body together with five video cameras to capture three dimensional motion data. Data can be captured during movement protocols that capture episodes of movement such as walking or a short series of repeated golf swings. Software that is part of the motion capture technology computes values of many variables comprising measures of linear and angular velocity and acceleration. Motion capture technology can result in extensive databases of high temporal resolution data with thousands of variables. Such databases are descriptive of particular episodes of movement for particular individuals.

ACPs can be computed from such databases. Such ACPs can show how every variable interacts with every other variable. ACPs for episodes of different behavior and for different individuals would be expected to have characteristics that could be assessed with morphometric analyses to identify salient features that distinguish various ACPs.

ACPs for movement will be used to illustrate coordination. Suppose that a particular movement protocol calls for a series of three repeated golf swings. It is anticipated that an expert golfer would have a well-defined ACP with many large magnitude scores. Such scores would indicate that particular movements are highly coordinated with other movements. Scores at specific values of delay would indicate precise sequences of movement. In contrast, the ACP of a novice golfer under the same conditions would be anticipated to be relatively flat. Movement sequences would not be as specific and repeatable.

ACPs also could be used to picture the effects of various interventions. Consider again the ACP of an expert golfer. Intoxication with a drug that alters behavior could be expected to flatten such a pro file.

ACPs can be used to investigate coordination for actions in addition to movement.

4.2.2. Physical and Electromagnetic Action

Physical and electromagnetic action involves properties that are part of the subject matter of physics. Included would be measures of pressure, flow, wavelength, intensity, and voltage. Some of the most interesting properties of complex systems appear to emerge from how basic physical actions are organized and interact.

Biological activity often is monitored with technologies such as electroencephalography and electrocardiography. Such procedures can yield many variables in the frequency and spatial domains. Such variables can be analyzed with ACPs.

4.2.3. Chemical or Biochemical Action

Changing levels or concentrations of chemicals can be measured repeatedly and may indicate chemical reactions or interactions. ACPs can be used to help investigate how such actions may be coordinated.

Biochemical reactions underlie much of the life sciences and medicine. Biologically active substances include endogenous products of gene expression such as hormones, neurotransmitters, receptors, and messenger molecules, as well as exogenous substances such as drugs and other chemical exposures. Many of the laboratory measures used in medicine reflect biochemical action.

4.2.4. Biological Action

Biological action becomes evident in living things. Although biological action includes physical and biochemical manifestations of living things, a new, more inclusive view of biological action is emerging. This is illustrated by the web site for the Institute of Systems Biology, "systems biology studies the complex interaction of all levels of biological information: DNA, mRNA, proteins, functional proteins, informational pathways and informational networks to understand how they work together."

The systems approach to biology can be contrasted with the more conventional approach that tends to investigate components of biological systems one by one. The systems approach explicitly recognizes that some of the most interesting and important properties of biological systems, such as immunity, are emergent or systems properties.

The systems approach to biology also can be applied to portions of biological systems. For example, attention, memory and learning can be considered as emergent or systems properties for brains or nervous systems.

MQALA can be applied most directly to physiological and environmental variables that can fluctuate in level over time and events that can recur for individuals. Although MQALA is not well suited to investigate structures themselves, MQALA can be applied to investigate how structures function.

4.2.5. Emotional, Mental, and Behavioral Action

Although many types of systems can be said to behave, this section focuses on psychology. The science of psychology investigates the behavior of animals and people, primarily for individuals as contrasted with groups. Psychology is considered to include investigations of emotional and mental action. As with biology, the subject matter of psychology usually has not been investigated as systems. MQALA, including ACPs, constitute a new set of analytic tools for investigating behavior and learning phenomena from a systems perspective.

Much of the subject matter in the psychology of learning can be considered to involve longitudinal associations (temporal contingencies) involving stimuli, responses, and reinforcers. Section 4.2.6 of the parent patent application includes major elements of an analysis of classical conditioning, operant conditioning, paired-associate learning, and associative learning in terms of changes in one type of longitudinal association in the presence of another type of longitudinal association. Furthermore, Section 4.2.6.4 of the parent application illustrates how such analyses can be applied to create artificial systems that learn. Artificial learning systems or robots can be considered as embodied models of learning systems.

Mental disorders are considered to involve emotional, mental, and behavioral action.

4.2.6. Social and Economic Action

Measures of social and economic action are a foundation for scientific investigations of collective entities such as societies and economies. Economic measures often are applied repeatedly to yield time series data that can be processed to construct ACPs.

4.2.7. Action Measurement Technologies

Major advances in sciences and disciplines such is medicine that apply science often depend on advances in measurement technologies. Some of these technologies are being singled out for special attention.

New measurement technologies tend to yield more data than people have been able to understand. This invention can help process much of this data to facilitate understanding of how complex systems function and interact. As such, this invention can increase the value of these measurement technologies by serving human needs.

4.2.7.1. Biochemical Measurement Technologies

New developments in biochemical measurement technology include microarrays or chips that can measure thousands of products of gene expression at one time. Any of these gene products may interact with any other gene product—interactions that may indicate up or down regulation of biochemical pathways or biopathways. Huge numbers of interactions can be investigated simultaneously when such chips and related procedures can be applied repeatedly and the resulting data are used to construct ACPs.

ACPs can be used to help quantify, discover, and describe protein-protein interactions. Quantification of protein-protein interactions would help make life sciences more productive. Discoveries and detailed descriptions made with ACPs could be objects of patent applications that identify biochemical pathways that may be new targets for drug development.

Furthermore, ACPs can be used to analyze protein-protein interactions. Section 4.8.9.2 describes how ACPs can be used alone and together with experimental procedures to help investigate the temporal criterion of causal and other predictive associations. Interactions can be analyzed as functions of analysis parameters used to construct ACPs. Interactions can be analyzed when operators such as AND, OR, NOR, XOR and NOT are applied to sets of independent and dependent events to define Boolean events. Such analyses can contribute to a detailed understanding of how organisms function.

Exogenous substances can be used as experimental probes to investigate biological systems. Here are two distinct and novel research strategies that involve the use of experimental probes and ACPs.

The first of these strategies would involve administration of the experimental probe repeatedly, possibly at various levels or doses, while many biochemicals are being measured at the same time. The resulting data would be used to construct ACPs that include the probe as a variable. This strategy would help reveal how the probe may interact with all the biochemicals.

The second of these two research strategies involves constructing ACPs under different treatment conditions, preferably for the same individuals. For example, separate ACPs can be constructed for the "on treatment" and the "off treatment" conditions. Differences in such ACPs would help reveal how treatment may affect any of many interactions portrayed in such ACPs. Unlike the first strategy, treatment would not be included as a variable in ACPs constructed with the second strategy.

The two research strategies just described are fundamentally different. The first strategy would reveal how treatment may affect levels of all the biochemicals. For example, the first strategy could help reveal how treatment may affect insulin and glucose levels.

In contrast, the second of these strategies would help reveal how treatment may affect any of the interactions between or among the biochemicals. For example, treatment may help restore a disordered interaction between insulin and glucose levels. Both research strategies could facilitate drug development by quantifying interactions that may indicate efficacy or possible safety concerns.

4.2.7.2. Functional Imaging

Functional magnetic resonance imaging and Positron Emission Tomography can measure biological activity in, for example, brains. Section 4.2.4 of the parent application explains how data from a series of such aligned images can be used to form serial pixel or serial region of interest variables. One such variable would correspond to each pixel or region of interest. Regions of interest could be delimited on the basis or shared structural or functional characteristics. Corresponding computational procedures could be applied to form serial voxel (volume element) variables.

ACPs can be computed using serial pixel, serial voxel, or serial region of interest variables and presented graphically as images. Such images would show how activity in each pixel, voxel, or region of interest interacts with activity in every other pixel or region of interest that is included in the ACP. Section 4.5 includes more information about portrayal of images and displays based on ACPs constructed from functional imaging data.

Functional connectivity within brains that is revealed by ACPs and derivative images could be investigated experimentally and non-invasively with transcranial magnetic stimulation of particular brain regions.

4.2.7.3. MicroElectroMechanical Systems (MEMS)

MEMS are super-miniaturized machines that can perform combinations of sensing, processing, communicating, and acting upon information. For example, so-called lab-on-a-chip MEMS are being developed that can operate from within human bodies.

MEMS will vastly increase amounts of time series data that can be analyzed with ACPs. This includes analyses that can be implemented within MEMS themselves.

4.2.7.4. Instrumentation for Psychophysics and Psychometrics

Psychometrics involves mental measurement. Psychophysics is concerned about the effects of physical processes such as wavelength and intensity on mental processes of organisms. Measurement technologies in these areas, many of which are computerized, help make the subject matter of psychology amenable to scientific investigations.

4.2.7.5. Performance Measures

Performance is measured in terms of things such as speed, accuracy, and skill. Computerized performance measurement technologies often are particularly well suited for yielding data that can be analyzed with ACPs.

4.2.7.6. Rating Scales and Surveys

Rating scales and surveys that often are based on self-report are benefiting from new measurement technologies that improve reliability, validity, and ease of use for many measures. For example, measures of health related quality of life are being developed that help provide a common metric for evaluating the effects of many treatment across many disorders.

Many rating scales and surveys can be applied repeatedly over the Internet. This facilitates the collection of repeated measures data that can be processed to construct ACPs.

4.2.8. Sciences and Disciplines

Major sciences and disciplines such as chemistry, biology, psychology, sociology, economics, and medicine can be considered to focus on certain combinations or clusters of objects and actions. As examples, psychology tends to focus on behavior of individual organisms. Medicine tends to focus on biochemical and behavioral signs and symptoms of individual organisms with health disorders.

The names of various sciences and disciplines are used to identify areas of application of MQALA including ACPs.

4.3. Computational Features

Various computational features of MQALA can be used to define independent and dependent events. These events are determined to be present or absent over different times thus forming dichotomous series or sets of dichotomous series used to compute ACPs. Table 1 lists section numbers of the parent application that describe these selected features. Section 4.4 of the parent application illustrates most of these features with an example.

TABLE 1

Computational features by section number in parent application.

| FEATURE | SECTION NUMBER OF PARENT APPLICATION |
|---|---|
| Variable level | 4.1.2 |
| Episode Length | 4.1.7 |
| Episode Criterion | 4.1.8 |
| Delay | 4.1.9 |
| Persistence | 4.1.10 |
| Boolean Events | 4.1.11 |
| Delay and Persistence After Boolean Events | 4.1.12 |
| Transition Events | 4.1.13 |
| Other Procedures Applied to Form Additional Dichotomous Series | 4.1.14 |

Variable level is a required analysis parameter when data for a variable are a dimensional series and users of MQALA select to investigate more than two levels of the variable. Episode length and episode criterion are optional analysis parameters that can be applied to define independent and/or dependent events. Delay and persistence are optional analysis parameters that can be applied to define independent events.

Boolean events and transition events can be applied to define independent events, dependent events, or both. Boolean events and transition events add columns and rows to dimensions of ACPs.

4.4. Measures Portrayed in ACPs

The parent application describes various measures that can be portrayed in ACPs. Parent application Section 4.1.1 describes how longitudinal association scores are computed. Parent application Section 4.1.5 describes how longitudinal association scores can be converted to benefit/harm scores for evaluation research. Parent application Section 4.1.6 describes computation of three related measures of strength of longitudinal association. Parent application Section 4.1.3 describes how longitudinal association scores and benefit/harm scores can be summarized. Analogous procedures can be used to summarize strength of longitudinal association measures.

4.5. Portrayal of ACPs

ACPs or portions of ACPs can be portrayed with various types of tables, figures, graphs, images, displays, or interactive displays. Section 4.9 of this application gives several examples of ACPs and portions of ACPs that are portrayed as tables. Such tables also can be portrayed graphically.

Portrayal of ACPs as images and displays will be illustrated in the context of functional imaging as described in Section 4.2.7.2. Such images and displays could be used to investigate functional connectivity of brain regions in ways that are useful for research and diagnosis. These images and displays could be color coded so that one range of colors represents degrees of excitatory activity (positive scores) and another range of colors represents degrees of inhibitory activity (negative scores).

ACPs derived from series of functional images can portray vast amounts of information. This is true, for example, when ACPs are computed from pixel or voxel data with one variable for each pixel or voxel. Such ACPs could have one row or column for each pixel or voxel functioning as an independent variable and one row or column for each pixel or voxel functioning as a dependent variable. However, such ACPs would not portray information in accordance with familiar anatomical shapes.

Functional connectivity of brain regions could be portrayed in accordance with familiar anatomical shapes by imaging or displaying ACP information one row or column at a time. This would yield a type of derivative image in which a particular pixel, voxel, or region of interest could be blank while measure values for all other cells in a column or row could be shown with color coding in there anatomically correct positions. Resulting images for particular brain regions would image functional connectivity of the particular regions with respect to all other regions included in the images.

The type of image just described could be portrayed in an interactive format. Suppose one wants to image functional interconnectivity using two-dimensional cross-sections of brains. Further suppose that one can use a cross-hair type pointer on a computerized image to identify a particular brain region. Once identified, the image would show how action in the particular region is associated with activity in every other region. For this type of interactive display, the required scores could either be stored in a potentially very large ACP or the required scores could be computed on demand.

4.6. Databases that Include ACPs

ACPs or portions of ACPs can be stored in databases, with or without additional data. Section 4.7 describes some ways in which these databases can be used.

4.7. Analyses of ACPs with Statistics or Other Quantitative Methods

ACPs are sets of measurements that can serve as input or be operated upon by statistics and other quantitative methods. Quantitative methods can be applied to individual ACPs, two or more ACPs for an individual, ACPs for two or more individuals, or portions of ACPs.

ACPs can be said to give shape to interactions. Shapes can be measured with morphometry.

ACPs can be analyzed statistically. For example, two or more ACPs with corresponding structures can be averaged. ACPs from two or more individuals can be used to describe groups or to make inferences about populations.

Science generally favors parsimonious explanations. Various quantitative methods such as factor analysis, discriminative analysis, and cluster analysis can be applied to ACPs. Such techniques, for example, can be applied to help reduce the number of variables that need to be measured while still capturing interactions that are of interest.

4.8. Uses of ACPs

MQALA, including ACPs, have many uses in addition to applications to various objects, actions, subject matters, and combinations thereof. The following subsections identify and describe some such uses. Together, such applications and uses form an extensive and varied tool kit for addressing problems involving repeated measures and time series data. Many problems are best addressed with time series data alone or in combination with cross-sectional data.

4.8.1. Use of ACPs to Measure Internal Control

ACPs that are constructed with variables that include two or more variables considered to be internal to the object represented by the ACP can be said to include measures of internal control. Terms used to describe internal control vary by scientific discipline. For example, some investigators speak of regulatory control in biological systems. In this context, the variables may measure endogenous substances such as hormones, neurotransmitters, messenger molecules, or other components of biochemical or signaling pathways. Internal control includes biochemical pathways or biopathways. Psychologists may use terms such as self-control.

Systems that include feedback or feed forward mechanisms often can be said to exhibit internal control.

4.8.2. Use of ACPs to Measure Responses to Environments

ACPs that are constructed with variables that include at least one variable in the environment of the object that is being represented by the ACP can be said to include measures of response to the environment. More specifically, those portions of such ACPs where environmental variable(s) function as independent variables portray responses to environments.

Treatments are an important subclass of environmental variables. Portions of ACPs that are responses to treatments generally would be portrayed with benefit/harm scores.

4.8.3. Use of ACPs to Measure Actions on Environments

Portions of ACPs corresponding to environmental variables functioning as dependent variables can be said to measure actions of objects represented by ACPs on their environments. In such cases, objects can be said to be functioning as agents acting on their environments.

4.8.4. Use of ACPs to Fingerprint Individuals

The section of this application that is titled "Brief Summary of the Invention" describes how ACPs can be used to fingerprint individual objects in terms of how they function or interact with their environments.

4.8.5. Use of ACPs to Portray Test Results

ACPs that portray test results can be descriptions of how their objects function and interact with their environments. Test results can be presented for many types of independent and dependent events simultaneously. Abnormal results on such tests could be diagnostic of disorders such as health disorders.

The tests from which ACP test results are obtained generally would be conducted under standardized conditions. Test conditions could be specified in test protocols. Test protocols would need to specify things such as type of object that is tested, variables used to construct ACPs and how they are to be measured, how any environmental variables would be controlled, all scoring features used to transform data and define events, as well as the type of measures portrayed in ACPs.

ACPs that result from tests could be accumulated in databases that include ACPs from many individuals. These databases could be analyzed to help distinguish normal from disordered test results and to classify individuals with distinct or disordered test results.

4.8.6. Use of ACPs to Identify Predictors of Disorder

Section 4.8.5 describes how ACPs can be used to portray test results that can in turn be analyzed to develop classifications of abnormal test results that indicate disordered functioning. Such classifications can be used to help identify predictors of disorder. For example, this approach could be used to search for single nucleotide polymorphisms that are predictive of abnormalities in the regulation of glucose metabolism.

4.8.7. Use of ACPs to Identify Predictors of Differential Response

ACPs that are based on multiple treatment and response variables can provide detailed descriptions of responses to treatments. Such ACPs for groups of patients can be used both to help classify responses to treatment and to help identify predictors of differential response. For example, this approach could be used to search for single nucleotide polymorphisms that are predictive of differential responses to drugs.

4.8.8. Use of ACPs to Measure Interactions Involving Different Types of Action Section 4.2 of this application illustrates several broad categories of action that can be investigated with ACPs. ACPs that are based on variables that measure different types of action can be used to investigate interactions involving actions of different types.

A number of scientific disciplines focus on interfaces between various types of action. Biochemistry is at the interface of chemistry and biology. Psychophysics is at the interface between physics and the psychology of perception. Social psychology is at the interface between behavioral and social action.

Section 1.2.2.2 illustrated hierarchies of measurement in the context of complexity. ACPs can be used to investigate interactions involving measures at different levels. For example, ACPs could be used to investigate interactions involving laboratory measures used in medicine and self-reported symptoms.

4.8.9. Use of ACPs to Help Distinguish Causal from Non-causal Associations

ACPs are quantitative descriptions of associations. ACPs generally portray how each type of event, defined on variables, is associated with every other type of event defined on the variables. Associations often do not indicate causal relationships.

Science often quests for causal relationships. MQALA and ACPs can be used to explore for causal relationships. In addition, MQALA and ACPs can be used together with the experimental method to help confirm causal relationships. Both strategies will be discussed in turn.

4.8.9.1. Exploring for Causal Relationships

MQALA and ACPs can use the analysis parameter called delay to help evaluate the temporal criterion of causal and other predictive relationships. Delay is defined on variables functioning as independent variables. It is more feasible to investigate delay with time series data in which measurements are obtained periodically after equal units of time.

The default value of delay is 0. When delay is set equal to 0, the associations that are measured are among events present at the same time. When delay is set equal to 1, associations involve dependent events occurring one time unit after independent events. Users generally would be able to select additional integer values of delay.

Typically the upper and lower portions of ACPs, as indicated by the symbols "o" and "*" respectively in Table 1, will not be symmetric, especially with nonzero values of delay. These asymmetries can be used to help investigate the temporal criterion of causal and other predictive associations. According to the temporal criterion, causes or predictors should come before effects or predicted events.

In the absence of any associations, all scores above or below a concordant diagonal in ACPs would be expected to hover around zero. This could be illustrated -by computing ACPs from data consisting of random numbers or random normal deviates.

An asymmetry can be illustrated simply with variables A and B. Suppose that the value of a strength of longitudinal association measure is substantially larger when Variable A functions as an independent variable and Variable B functions as a dependent variable than vice versa. This would indicate that Variable A is a stronger predictor of Variable B than Variable B is a predictor of Variable A. In general, large asymmetries would provide more revealing information about the direction of causal and other predictive associations. Asymmetries also can be examined for Boolean events.

Figure 2:
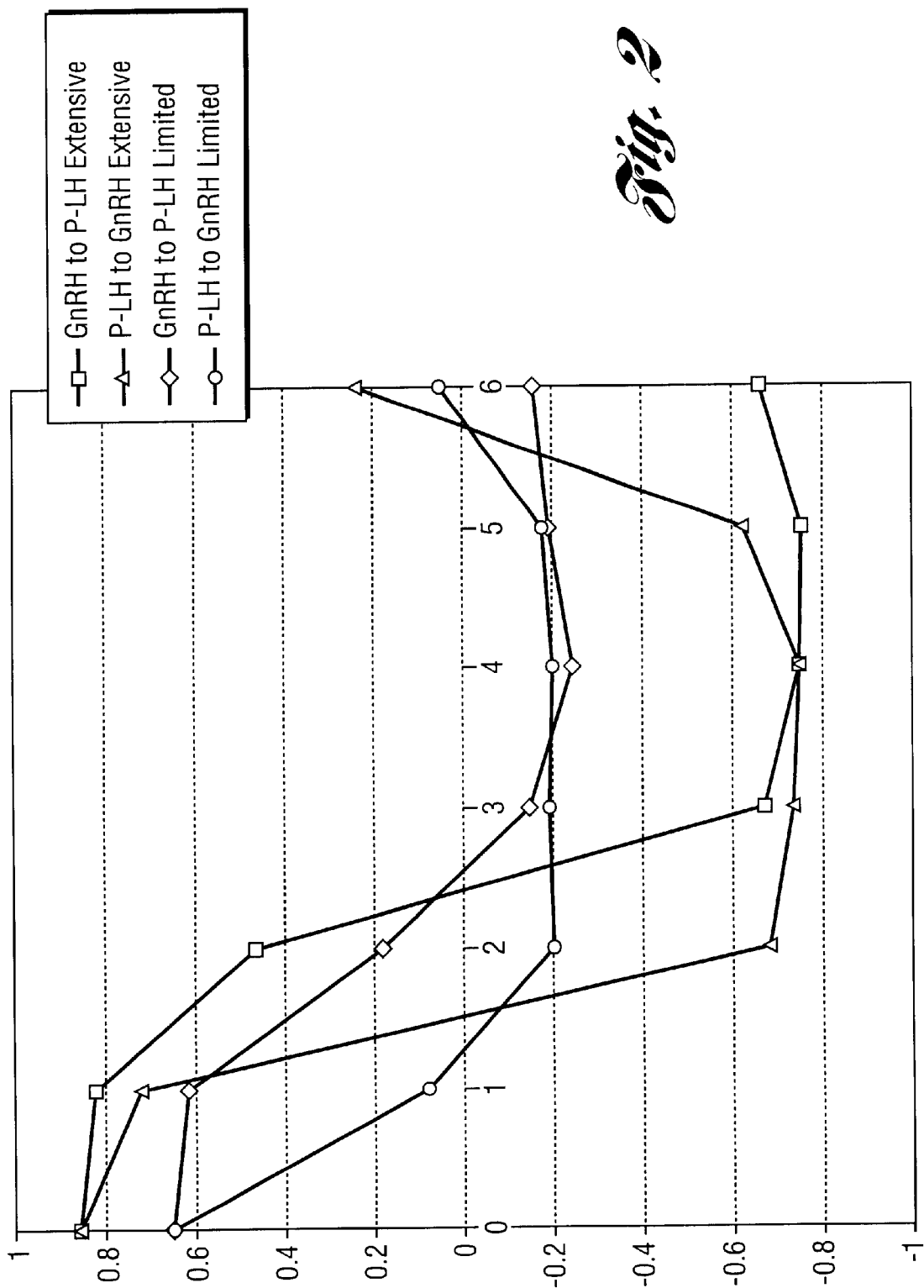
FIG. 2 portrays average strength of a longitudinal association measure as a function of delay for interactions involving GnRH and P-LH.
Figure 3:
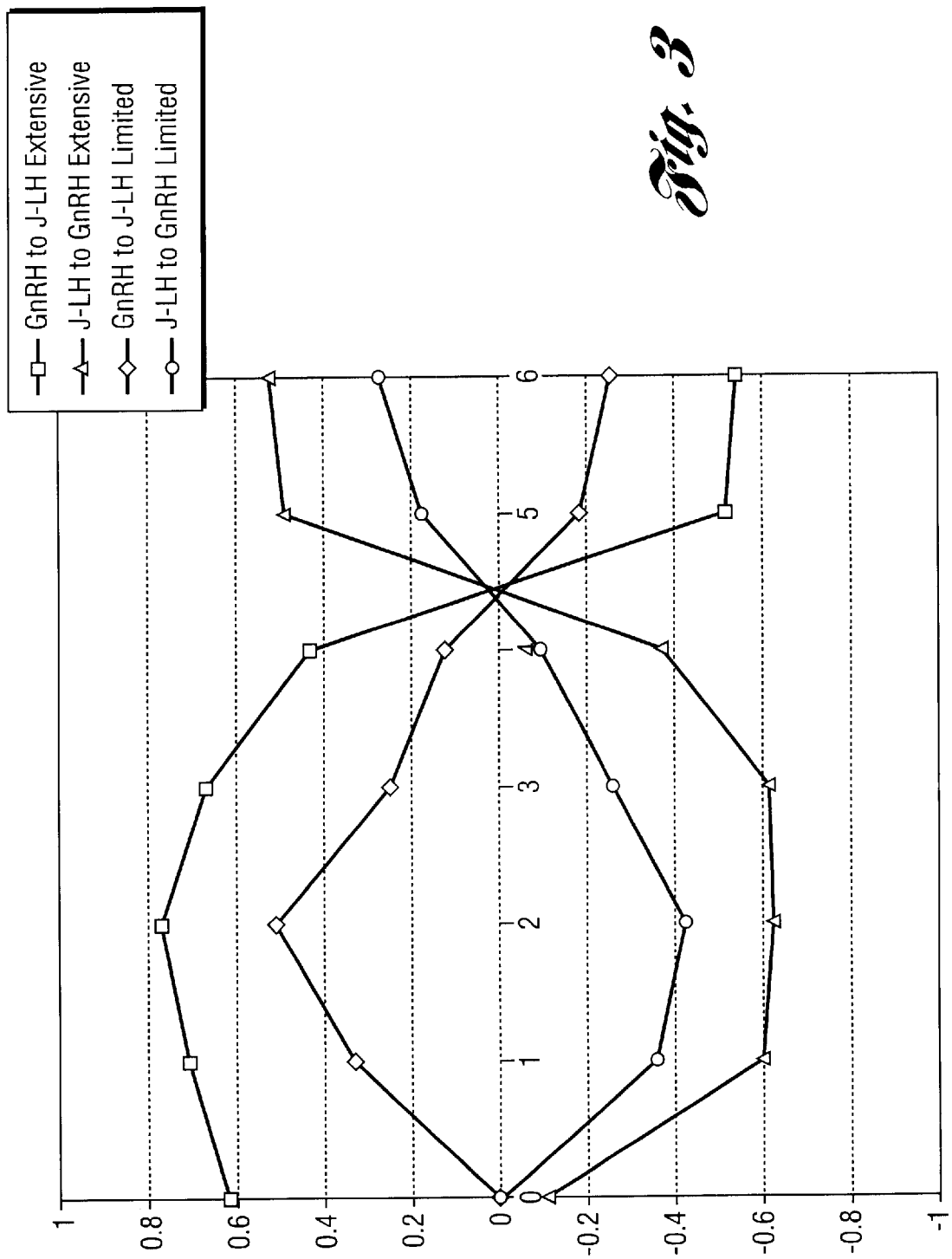
FIG. 3 portrays average strength of a longitudinal association measure as a function of delay for interactions involving GnRH and J-LH.

Asymmetries in ACPs can be examined in different ways. FIGS. 2 and 3, further described in Section 4.9, illustrate asymmetries using data from reproductive endocrinology.

Asymmetry tables or graphs, which are computed from ACPs, can be used to investigate the temporal criterion. One way to construct an asymmetry table or graph is to subtract values from one portion of an ACP from corresponding values in the other portion of the ACP. Asymmetry with respect to, for example, the cell corresponding to IV 6 and DV 3 can be examined by subtracting the value in this cell from the value in the cell corresponding to IV 3 and DV 6.

ACPs and asymmetry tables or graphs are useful tools for exploratory data analyses that involve causal or other predictive associations. This type of exploratory data analysis or data mining can be conducted using ACPs that summarize across a range of nonzero positive values of delay. Such ACPs show how each variable may be associated to each other variable in a single ACP or asymmetry table or graph.

In addition, the temporal criterion of causal or other predictive associations can be investigated using a series of ACPs and asymmetry tables or graphs that summarize and quantify associations as functions of various values of delay.

A series of delay specific ACPs and asymmetry tables or graphs can be used to investigate cascades of events in complex systems. For example one variable may be associated with increases or decreases in a second variable after some delay. In turn increases or decreases in the second variable may be associated with increases or decreases in a third variable after some additional delay. In general, more delayed effects are apt to be weaker because they are mediated by a series of more immediate effects that may dampen more delayed effects. It also appears that ACPs and asymmetry tables can be used to investigate positive and negative feedback loops.

The next section describes how MQALA and ACPs can be applied to experimental data to help confirm causal relationships. However, for some individuals such as large-scale economic or environmental systems, it may not be feasible to conduct experiments that require isolation of independent variables. For such individuals, it may be more feasible to investigate causality by applying MQALA and ACPs with wide ranges of scoring options and data that are as comprehensive (measure many relevant variables) and detailed (avoid composite variables) as feasible. In addition, it generally would be advantageous for the repeated measurements to be collected periodically, frequently, and often over long periods of time.

4.8.9.2. Confirming Causal Relationships

Scientists often use experiments in attempts to confirm causal relationships. Experimental strategies and procedures include randomization; isolation of independent variables; and blinding of subjects, observers, and data analysts.

MQALA is entirely compatible with such strategies and procedures when they are applied during data collection. In fact, MQALA often enables new ways of applying such strategies and procedures by expanding the range of types of data that can be analyzed effectively by computational procedures. For example, MQALA often helps make it feasible to randomize doses of treatment to different time periods for individual patients. In addition, two or more dose levels (which may or may not include a placebo dose of zero) can be used for each patient.

The conventional experimental strategy that often is applied in conjunction with the statistical method is to assign individuals to separate groups such as treated and untreated patients. An alternative strategy that is facilitated by MQALA is to control variable input signals for individuals to examine how a host of other variables interact with the signal. ACPs for two or more individual subjects could then be analyzed statistically.

4.8.10. Use of ACPs for Data Mining

Section 4.2.1.2 of the parent application describes the application of MQALA to data mining. Section 1.1 of this application describes the interactions that ACPs quantify as becoming evident as patterns in repeated measures and time series data. ACPs can be used to mine for such patterns.

ACPs can be a major tool for discovery science as described in Section 1.2.2.4.

4.8.11. Use of ACPs for Nested Systems

Section 4.1.7 illustrates nested systems and how they can be investigated with ACPs. ACPs can be important tools for investigating interactions involving physical or conceptual entities with different degrees of inclusiveness.

4.8.12. Use of ACPs to Distinguish Episodes of Action

As described in Section 2, scientific investigations need to be limited in scope. As illustrated in this application, particular ACPs are limited to particular types of action measured by particular variables for particular types of objects. Another crucial way to limit scope is to limit ACPs to particular episodes of action.

Walk, cantor, trot, and gallop illustrate episodes of locomotion for horses. Similarly, episodes can be distinguished for different types of action. MQALA includes tools for helping to distinguish episodes of action.

Section 4.1.15 of the parent application describes sequential analysis of longitudinal association scores and strength of longitudinal association measures. Sequential analysis also can be called iterative analysis.

Sequential or iterative analysis also can be applied to ACPs. With this procedure, ACPs would be constructed sequentially over measurement occasions. Measure values for corresponding locations in ACPs can be plotted as functions of time or measurement occasion. Such graphs could be analyzed by looking for inflections or sets of inflections to help distinguish different episodes.

4.8.13. Use of ACPs for Model Development and Testing

As described in Section 1.2, scientific knowledge often is represented in the form of mathematical models. ACPs can be used to inform the model development process. ACPs also can be used to test dynamic models by comparing ACPs produced by models with ACPs for the objects and actions modeled.

4.8.14. Use of ACPs to Draw Generalized Conclusions and to Make Predictions This application is a child of the parent application with the title "Computational Method and System to Perform Empirical Induction." Empirical induction was defined as involving drawing generalized conclusions and making predictions from data. As such, drawing generalized conclusions and making predictions are inventive and important uses of ACPs.

Section 1.2 of the parent application presents four criteria for high quality generalized conclusions and predictions. ACPs can be used as tools to help draw high quality generalized conclusions and to make high quality predictions.

4.8.15. Use of ACPs to Make Scientific Discoveries

Advances in technology for measuring actions have far outstripped our ability to make scientific discoveries based on how actions interact. MQALA, including ACPs, address this problem by measuring interactions with computational methods and systems.

4.8.16. Use of ACPs to Guide Decision-Making

Section 2.8.2 of the parent application describes how MQALA can be used from a practical perspective in the context of decision-making. Similar arguments apply to this improvement on MQALA, ACPs.

4.9. Examples of ACPs

Tables 2 through 5 and FIGS. 2 and 3 are based on data from reproductive endocrinology. For these tables and figures, the objects of investigation are ewes, the actions involve hormones, and the use is to investigate internal control.

The data for Tables 2 through 5 and FIGS. 2 and 3 are described and reported in two publications: Padmanabhan, V., McFadden, K., Mauger, D. T., Karsch, F. J., and Midgley, A. R. (1997). Neuroendocrine control of follicle-stimulating hormone (FSH) secretion. 1. Direct evidence for separate episodic and basal components of FSH secretion. *Endocrinology* 138, 424–432 and Midgley, A. R., McFadden, K., Ghazzi, M., Karsch, F. J., Brown, M. R., Mauger, D. T., and Padmanabhan, V. (1997). Nonclassical secretory dynamics of LH revealed by hypothalamo-hypophyseal portal sampling of sheep. *Endocrine* 6, 133–143. The authors kindly provided access to data described by these publications.

Tables 2 through 4 are based on data for one ewe. Data for these tables were obtained by assessing five hormone measures every 5 minutes for about 12 hours—143 repeated measurements of each measure. The hormone measures are gonadotropin releasing hormone (GnRH), portal luteinizing hormone (P-LH), jugular luteinizing hormone, portal follicle stimulating hormone (P-FSH), and jugular follicle stimulating hormone (P-FSH). Portal measures were obtained from blood sampled near the pituitary gland.

Table 2 and Table 4 each portray an ACP. The scoring protocol for Tables 2 and 4 is, in brief, as follows. The set of dichotomous series for each variable was formed by first computing the standardized residuals from its linear regression line on time or measurement number. Next, intervals of z-scores for the residuals were used to form 12 dichotomous series for each variable.

In addition, the scoring protocol for Tables 2 and 4 used optional values of additional analysis parameters. Ten combinations of episode length and episode criterion were applied to variables functioning as independent variables and to variables functioning as dependent variables. These 10 combinations resulted from applying episode length values 1 through 4 and all values of episode criterion that are possible given these values of episode length. Delay values of 0, 1, and 2 and persistence values of 1 and 2 were applied whenever a variable functioned as an independent variable. Table 1 identifies sections of the parent application that describe these analysis parameters.

Table 2 portrays summary longitudinal association scores. Table 2 includes summaries of three delay-specific portions of an ACP plus a summary of the entire ACP. The summary of the entire ACP is summarized across the three delay-specific portions of the ACP.

Each score in the delay specific sections of Table 2 is summarized across 28,800 delay specific longitudinal association scores. The number 28,800 is the product of 12 levels of the independent variable, 12 levels of the dependent variable, 10 combinations of episode length and criterion for the independent variable, 10 combinations of episode length and criterion for the dependent variable, and 2 levels of persistence. Each summary score in the summary ACP portion of Table 2 is summarized across 86,400 scores (3 times the 28,800 delay-specific scores).

Table 2 is a particular portrayal of the entire ACP constructed from the hormone data and with the scoring protocol described earlier in this section. The entire ACP includes 1,728,000 longitudinal association scores—86,400 for each of the 20 interactions. Each of interactions is evaluated with respect to 8 dimensions that correspond to analysis parameters.

The first score in Table 2, the summary score for the interaction between GNRH functioning as the independent variable and P-LH functioning as the dependent variable, is 76.728. This score is one score from a distribution of scores with a mean of zero and a standard deviation of 1. The distribution consists of all 47 scores that are possible given the marginal frequencies of the 2×2 table from which the score was computed. The 2×2 table resulted from the cross-classification of a particular member of the set of dichotomous series representing the independent variable with a particular member of the set of dichotomous series representing the dependent variable.

The distribution of longitudinal association scores that includes 76.728 is shown in Table 3. The magnitude of this score (76.728), shown in bold at the bottom of Table 3, indicates that there is much evidence for a longitudinal association between GNRH and P-LH. Furthermore, the association is positive—high levels of GnRH are associated with high levels of P-LH. Section 4.1.1 of the parent application shows how cells of the 2×2 table are labeled and how longitudinal association scores are computed.

Each interaction portrayed in Table 2 could be investigated in detail by examining all or subsets of the longitudinal association scores that are summarized. This includes examination of interactions as functions of any or all of the analysis parameter levels used in the analysis. The location of the summary score in the array of scores that was summarized identifies levels of all analysis parameters that yield the most evidence for the longitudinal association.

TABLE 2

A portrayal of the ACP for the hormone data that uses summary longitudinal association scores.

| Independent Variable | Dependent Variable | | | | |
|---|---|---|---|---|---|
| | GnRH | P-LH | J-LH | P-FSH | J-FSH |
| Summary of the Delay = 0 Specific Portion of the ACP | | | | | |
| GnRH |  | 76.728 | 47.287 | 62.909 | 22.472 |
| P-LH | 76.165 |  | 48.329 | 74.014 | −15.312 |
| J-LH | 36.773 | 41.970 |  | 28.605 | 19.569 |
| P-FSH | 61.014 | 74.014 | 37.956 |  | 16.684 |
| J-FSH | 16.503 | −15.533 | 19.253 | 11.900 |  |
| Summary of the Delay = 1 Specific Portion of the ACP | | | | | |
| GnRH |  | 73.359 | 52.844 | 47.991 | 31.574 |
| P-LH | 64.184 |  | 53.892 | 47.755 | 28.745 |
| J-LH | −31.888 | 34.509 |  | −27.607 | 19.569 |
| P-FSH | 50.764 | 51.684 | 48.622 |  | 24.488 |
| J-FSH | −19.005 | −19.741 | 19.529 | −16.764 |  |
| Summary of the Delay = 2 Specific Portion of the ACP | | | | | |
| GnRH |  | 42.142 | 52.337 | 28.408 | 33.838 |
| P-LH | −37.334 |  | 51.378 | 28.724 | 28.883 |
| J-LH | −31.888 | 31.184 |  | −28.221 | 16.506 |
| P-FSH | −34.891 | −33.156 | 44.837 |  | 31.971 |
| J-FSH | −20.389 | −24.279 | −14.492 | −21.441 |  |
| Summary of the Entire ACP | | | | | |
| GnRH |  | 76.728 | 52.844 | 62.909 | 33.838 |
| P-LH | 76.165 |  | 53.892 | 74.014 | 28.883 |
| J-LH | 36.773 | 41.970 |  | 28.605 | 19.569 |
| P-FSH | 61.014 | 74.014 | 48.622 |  | 31.971 |
| J-FSH | −20.389 | −24.279 | 19.529 | −21.441 |  |

TABLE 3

Distribution of longitudinal association scores that includes 76.728.

| Cell Frequencies | | | | Longitudinal | |
|---|---|---|---|---|---|
| A | b | c | d | Association Score | Probability |
| 0 | 46 | 48 | 48 | −20.015 | 3.22270e-11 |
| 1 | 45 | 47 | 49 | −17.525 | 1.45219e-9 |
| 2 | 44 | 46 | 50 | −15.199 | 3.07138e-8 |
| 3 | 43 | 45 | 51 | −13.039 | 4.06305e-7 |
| 4 | 42 | 44 | 52 | −11.045 | 3.77981e-6 |
| 5 | 41 | 43 | 53 | −9.216 | 2.63588e-5 |
| 6 | 40 | 42 | 54 | −7.553 | 0.000143428 |
| 7 | 39 | 41 | 55 | −6.055 | 0.000625867 |
| 8 | 38 | 40 | 56 | −4.723 | 0.00223384 |
| 9 | 37 | 39 | 57 | −3.556 | 0.00661879 |
| 10 | 36 | 38 | 58 | −2.555 | 0.0164671 |
| 11 | 35 | 37 | 59 | −1.719 | 0.0347103 |
| 12 | 34 | 36 | 60 | −1.049 | 0.0624304 |
| 13 | 33 | 35 | 61 | −0.544 | 0.0963616 |
| 14 | 32 | 34 | 62 | −0.205 | 0.128223 |
| 15 | 31 | 33 | 63 | −0.032 | 0.147626 |
| 16 | 30 | 32 | 64 | 0.010 | 0.147482 |
| 17 | 29 | 31 | 65 | 0.168 | 0.128129 |
| 18 | 28 | 30 | 66 | 0.490 | 0.0969597 |
| 19 | 27 | 29 | 67 | 0.979 | 0.0639797 |
| 20 | 26 | 28 | 68 | 1.633 | 0.0368354 |
| 21 | 25 | 27 | 69 | 2.452 | 0.0185067 |
| 22 | 24 | 26 | 70 | 3.437 | 0.00811169 |
| 23 | 23 | 25 | 71 | 4.587 | 0.00309963 |
| 24 | 22 | 24 | 72 | 5.903 | 0.00103142 |
| 25 | 21 | 23 | 73 | 7.385 | 0.000298404 |
| 26 | 20 | 22 | 74 | 9.032 | 7.49112e-5 |

TABLE 3-continued

Distribution of longitudinal association scores that includes 76.728.

| Cell Frequencies | | | | Longitudinal | |
|---|---|---|---|---|---|
| A | b | c | d | Association Score | Probability |
| 27 | 19 | 21 | 75 | 10.844 | 1.62770e-5 |
| 28 | 18 | 20 | 76 | 12.822 | 3.05194e-6 |
| 29 | 17 | 19 | 77 | 14.966 | 4.92028e-7 |
| 30 | 16 | 18 | 78 | 17.275 | 6.79166e-8 |
| 31 | 15 | 17 | 79 | 19.749 | 7.98693e-9 |
| 32 | 14 | 16 | 80 | 22.389 | 7.95573e-10 |
| 33 | 13 | 15 | 81 | 25.195 | 6.66698e-11 |
| 34 | 12 | 14 | 82 | 28.166 | 4.66306e-12 |
| 35 | 11 | 13 | 83 | 31.302 | 2.69671e-13 |
| 36 | 10 | 12 | 84 | 34.604 | 1.27523e-14 |
| 37 | 9 | 11 | 85 | 38.072 | 4.86574e-16 |
| 38 | 8 | 10 | 86 | 41.705 | 1.47402e-17 |
| 39 | 7 | 9 | 87 | 45.504 | 3.47543e-19 |
| 40 | 6 | 8 | 88 | 49.468 | 6.22023e-21 |
| 41 | 5 | 7 | 89 | 53.597 | 8.18226e-23 |
| 42 | 4 | 6 | 90 | 57.893 | 7.57617e-25 |
| 43 | 3 | 5 | 91 | 62.353 | 4.64677e-27 |
| 44 | 2 | 4 | 92 | 66.979 | 1.72188e-29 |
| 45 | 1 | 3 | 93 | 71.771 | 3.29152e-32 |
| 46 | 0 | 2 | 94 | 76.728 | 2.28366e-35 |

Table 4 is the same as Table 2 except that Table 4 portrays values of summary strength of longitudinal association measures rather than summary longitudinal association scores. The strength measure used in Table 4 is the measure labeled SD in Section 4.1.6 of the parent application. Section 4.1.6 of the parent application also describes computation of values of the strength of longitudinal association measures.

Table 4 portrays a different ACP than that portrayed in Table 2 in that the two ACPs use different measures of longitudinal association or temporal contingency.

TABLE 4

A portrayal of the ACP for the hormone data that uses values of a summary strength of longitudinal association measure.

| Independent Variable | Dependent Variable | | | | |
|---|---|---|---|---|---|
| | GnRH | P-LH | J-LH | P-FSH | J-FSH |
| Summary of the Delay = 0 Specific Portion of the ACP | | | | | |
| GnRH | | .938 | .587 | .782 | .297 |
| P-LH | .938 | | .600 | .912 | −.190 |
| J-LH | .456 | .534 | | .356 | .243 |
| P-FSH | .758 | .912 | .471 | | .207 |
| J-FSH | .215 | −.191 | .237 | .148 | |

TABLE 4-continued

A portrayal of the ACP for the hormone data that uses values of a summary strength of longitudinal association measure.

| Independent Variable | Dependent Variable | | | | |
|---|---|---|---|---|---|
| | GnRH | P-LH | J-LH | P-FSH | J-FSH |
| Summary of the Delay = 1 Specific Portion of the ACP | | | | | |
| GnRH | | .911 | .660 | .596 | .482 |
| P-LH | .797 | | .673 | .587 | .360 |
| J-LH | −.396 | .446 | | −.346 | .243 |
| P-FSH | .630 | .635 | .608 | | .307 |
| J-FSH | −.234 | −.243 | .283 | −.210 | |
| Summary of the Delay = 2 Specific Portion of the ACP | | | | | |
| GnRH | | .523 | .658 | .353 | .427 |
| P-LH | −.469 | | .645 | .356 | .364 |
| J-LH | −.396 | .397 | | −.351 | .204 |
| P-FSH | −.438 | −.416 | .565 | | .400 |
| J-FSH | −.253 | −.301 | −.182 | −.270 | |
| Summary the Entire ACP | | | | | |
| GnRH | | .938 | .660 | .782 | .427 |
| P-LH | .938 | | .673 | .912 | .364 |
| J-LH | .456 | .534 | | .356 | .243 |
| P-FSH | .758 | .912 | .608 | | .400 |
| J-FSH | −.253 | −.301 | .283 | −.270 | |

Table 5 demonstrates a statistical analysis of a summary measure of strength of longitudinal association. The values in Table 5 are for four associations and six ewes. Labels such as "GnRH to P-LH" indicate that GnRH is functioning as the independent variable and P-LH is functioning as the dependent variable. Table 5 includes the value of the first strength of longitudinal association measure in Table 4. It is for Ewe 3 and is shown in bold in Table 5.

Note that in Table 5, statistical tests are being performed on values of a summary strength of longitudinal association measure rather than measures of the hormones themselves. The statistical test for any particular association is based on only one value for each ewe. The null hypothesis is that there is no longitudinal association between variables, that the mean score equals zero. The statistical tests are single group t-tests on the means. All p-values are for two-tailed tests.

The values for individual ewes in Table 5 are conclusions, generalized across up to 143 repeated measurements of each variable for each ewe, about certain longitudinal associations for each ewe. The means and standard deviations (S.D.) describe the associations for a group of six ewes. Assuming that the group is a representative sample of some population of ewes, the results of the statistical tests apply most directly to a collective entity, namely, the population of ewes rather than any particular ewe.

TABLE 5

Statistical analyses of values of a summary strength of longitudinal association measure for 6 ewes.

| Association | Ewe | | | | | | Mean | S.D. | p |
|---|---|---|---|---|---|---|---|---|---|
| | 1 | 2 | 3 | 5 | 6 | 10 | | | |
| GnRH to P-LH | 0.879 | 0.881 | 0.938 | 0.878 | 0.734 | 0.826 | 0.856 | 0.070 | <.0001 |
| GnRH to J-LH | 0.770 | 0.647 | 0.660 | 1.000 | 0.684 | 0.854 | 0.769 | 0.138 | <.0001 |
| GnRH to P-FSH | 0.593 | 0.652 | 0.782 | 0.669 | 0.489 | 0.251 | 0.572 | 0.185 | .0006 |
| GnRH to J-FSH | 0.450 | 0.375 | 0.427 | 0.871 | 0.671 | 1.000 | 0.632 | 0.259 | .0019 |

FIGS. 2 and 3 also are based on the hormone data. These figures demonstrate the use of ACPs to evaluate the temporal criterion of causal and other predictive relationships. Both figures show average values of a summary strength of longitudinal association measure in which the averages are obtained across the six ewes identified in Table 5. The group average value of a summary strength of longitudinal association measure is shown as functions of the analysis parameter called delay.

FIG. 2 portrays associations involving GnRH and P-LH in which both hormone measures function as both independent and dependent variables. The key that identifies lines in FIG. 2 includes reference to "Extensive" and "Limited." These labels refer to scoring options used in two scoring protocols. Scores based on the protocol labeled "Extensive" were the same as those described in paragraphs 3 and 4 of this section except for additional values of delay (a total of 7 values of delay, 0 through 6). In contrast, scores labeled "Limited" are based on a protocol that used default values for episode length, episode criterion, and persistence.

FIG. 2 helps validate a new methodology (MQALA and ACPs) by confirming that the new methodology reveals a known relationship—namely that GnRH secretion largely controls P-LH secretion. First, FIG. 2 shows clear patterns in average strength of longitudinal associations between GnRH and P-LH as a function of delay. The most extreme values are positive and are for delay equals zero. Furthermore, the curves for the P-LH to GnRH interactions appear to be shifted to the left relative to the corresponding GnRH to P-LH interactions. Together, these results suggest that GnRH secretion tends to elicit P-LH secretion in a manner that is relatively rapid compared to the temporal resolution of these data—the temporal resolution being 5 minutes.

Results for delay equals 4 are among the most extreme negative average summary strength of longitudinal association measure values shown in FIG. 2. This indicates that high levels of the independent variable are associated with low levels of the dependent variable about 20 minutes latter. The interactions portrayed in FIG. 2 tend to be periodic.

FIG. 2 also shows that values of the average summary strength of longitudinal association measure that are obtained with the "extensive" scoring protocol options are more extreme (closer to the maximum values of plus or minus 1) than corresponding values obtained with the "limited" options. This suggests that the optional levels of the analysis parameters called episode length, episode criterion, and persistence do account for additional systematic variation in the data.

FIG. 3 was obtained in the same manner as FIG. 2 except that luteinizing hormone was measured in jugular blood rather than portal blood. High levels of GnRH are associated most strongly with high levels of J-LH about 10 minutes later as these variables were measured in these investigations. As indicated by the difference between the "extensive" and the "limited" options for values of the average summary strength of longitudinal association measure for the GnRH to J-LH interaction at delay zero; episode length, episode criterion, and persistence can tend to blur results for delay. However, these additional analysis parameters do tend to account for more systematic variation in the data as indicated by more extreme positive and negative values.

Although Tables 2 through 5 and FIGS. 2 and 3 portray interactions involving only five hormone variables, these examples illustrate how this invention could be used to explore, discover, and confirm thousands or millions of interactions involving hundreds or thousands of products of gene expression including proteins. Many of the computational procedures could be automated. As such, this invention can be an important and valuable contribution to bioinformatics. Furthermore, this invention can be applied to objects of investigation that are of other types as illustrated with Table 6.

Table 6 is an ACP that portrays internal control of the United States economy. The action involves ten variables used to obtain values of the Index of Leading Economic Indicators, one variable that is a measure of the Gross Domestic Product of the United States economy, and one variable that is the Index of Leading Economic Indicators. The data were obtained from The Conference Board and are for 169 consecutive quarters ending recently.

The scoring protocol for Table 6 involves using residuals from second order polynomial regression of each variable on measurement occasion and 12 dichotomous series to represent levels of each variable. Table 6 is for delay equals 2. Default values were used for episode length, episode criterion, and persistence. Table 6 portrays summary strength of longitudinal association scores.

TABLE 6

A delay-equals-2-specific ACP for the United States economy.

| Independent Variable* | Dependent Variable* | | | | | | | | | | | |
|---|---|---|---|---|---|---|---|---|---|---|---|---|
| | GDP | MfHrs | Unemp | MfCG | Vend | MfCap | Bldg | Stock | Money | Rate | CsExp | LEI |
| GDP | | .041 | −.262 | .372 | .132 | .448 | .104 | .437 | .318 | −.384 | .178 | .408 |
| MfHrs | .149 | | −.369 | .239 | .356 | .108 | .119 | .102 | .176 | −.162 | .163 | .239 |
| Unemp | −.475 | −.222 | | −.455 | −.172 | −.241 | −.193 | −.240 | −.230 | .277 | −.139 | −.316 |
| MfCG | .593 | .120 | −.352 | | .207 | .687 | .185 | .603 | .222 | −.351 | −.161 | .340 |
| Vend | .131 | .184 | −.254 | .268 | | .183 | .140 | .095 | .112 | −.160 | .074 | .176 |
| MfCap | .463 | −.061 | −.146 | .448 | .110 | | .109 | .673 | .101 | −.399 | −.233 | .143 |
| Bldg | .311 | .178 | −.350 | .331 | .214 | .259 | | .229 | .212 | −.139 | .152 | .324 |
| Stock | .529 | −.066 | −.154 | .503 | .102 | .609 | .275 | | .257 | −.188 | .199 | .388 |
| Money | .257 | .121 | −.258 | .233 | .097 | .213 | .114 | .102 | | −.082 | .161 | .367 |
| Rate | −.164 | .148 | .081 | −.064 | .120 | −.190 | .120 | −.172 | .115 | | .208 | .207 |

TABLE 6-continued

A delay-equals-2-specific ACP for the United States economy.

| Independent Variable* | Dependent Variable* | | | | | | | | | | | |
|---|---|---|---|---|---|---|---|---|---|---|---|---|
| | GDP | MfHrs | Unemp | MfCG | Vend | MfCap | Bldg | Stock | Money | Rate | CsExp | LEI |
| CsExp | .338 | .259 | −.289 | .246 | .131 | .106 | .238 | .180 | .415 | .119 | | .584 |
| LEI | .547 | .361 | −.532 | .354 | .262 | .282 | .238 | .301 | .543 | −.151 | .329 | |

*Abbreviations for the variables are as follows: GDP = Gross Domestic Product; MfHrs = Average weekly hours, manufacturing; Unemp = Average weekly initial claims for unemployment insurance; MfCG = Manufacturers' new orders, consumer goods and materials; Vend = Vendor performance, slower deliveries diffusion index; MfCap = Manufacturers' new orders, non-defense capital goods; Bldg = Building permits, new private housing units; Stock = Stock prices, 500common stocks; Money = Money supply, M2; Rate = Interest rate spread, 10-year Treasury bonds less federal funds; CsExp = Index of consumer expectations; LBI = Leading Economic Index.

Interpretation of Table 6 will be illustrated with the dependent variable column labeled GDP. Independent variables labeled MfCG, Stock, MfCap, and CsExp are the most powerful predictors of GDP, given these data and the particular scoring protocol used for Table 6. The independent variables labeled Unemp and Rate are negatively associated with GDP. As expected, LEI is positively predictive of GDP.

While the best mode for carrying out the invention has been described in detail, those familiar with the art to which this invention relates will recognize various alternative designs and embodiments for practicing the invention as defined by the following claims.

APPENDIX
Outline of Application

1. BACKGROUND OF THE INVENTION
    1.1. Technical Field
    1.2. Description of Related Art
        1.2.1. The Need to Measure Interactions that are Temporal Contingencies
        1.2.2. Specific Problems Involved in the Prior Art
            1.2.2.1. Problems Involving Individuality
            1.2.2.2. Problems Involving Complexity
            1.2.2.3. Problems Involving Nonlinearity
            1.2.2.4. Problems Involving Comprehensiveness
            1.2.2.5. Problems Involving Detail
            1.2.2.6. Need to Investigate All Five Types of Problem as a Set
        1.2.3. Citations
2. BRIEF SUMMARY OF THE INVENTION
    2.1. Structure of ACPs
    2.2. Functions of ACPs
    2.3. How do ACPs Help Address Limitations of the Statistical Method?
        2.3.1. MQALA and the Statistical Method Are Best Suited to Analyze Distinct Types of Data (Evidence)
        2.3.2. MQALA and the Statistical Method Have Distinct Objectives
        2.3.3. MQALA and the Statistical Method Use Distinct Computational Procedures
        2.3.4. MQALA and the Statistical Method Are Best Suited for Distinct Types of Entities
    2.4. MQALA Helps Address Problems Described in Section 1.2.2.
        2.4.1. ACPs Help Address Problems Involving Individuality
        2.4.2. ACPs Help Address Problems Involving Complexity
        2.4.3. ACPs Help Address Problems Involving Nonlinearity
        2.4.4. ACPs Help Address Problems Involving Comprehensive Investigations
        2.4.5. ACPs Help Address Problems Involving Detailed Investigations
        2.4.6. Addressing the Need to Investigate All Five Types of Problem as a Set APPENDIX
Outline of Application 3. BRIEF DESCRIPTION OF THE SEVERAL VIEWS OF THE DRAWING
4. DETAILED DESCRIPTION OF THE INVENTION
    4.1. Objects of Investigation and Their Environments
        4.1.1. Organisms Including Persons
        4.1.2. Portions of organisms
        4.1.3. Economies and Investment Markets
        4.1.4. Machines, Processes, and Other Man Made Systems
        4.1.5. Systems Consisting of Two or More Individuals
        4.1.6. Populations Investigated as Wholes
        4.1.7. Nested Systems
        4.1.8. Additional Types of Systems
    4.2. Actions
        4.2.1. Movement
        4.2.2. Physical and Electromagnetic Action
        4.2.3. Chemical or Biochemical Action
        4.2.4. Biological Action
        4.2.5. Emotional, Mental, and Behavioral Action
        4.2.6. Social and Economic Action
        4.2.7. Action Measurement Technologies
            4.2.7.1. Biochemical Measurement Technologies
            4.2.7.2. Functional Imaging
            4.2.7.3. MicroElectroMechanical Systems (MEMS)
            4.2.7.4. Instrumentation for Psychophysics and Psychometrics
            4.2.7.5. Performance Measures
            4.2.7.6. Rating Scales and Surveys
        4.2.8. Sciences and Disciplines
    4.3. Computational Features
    4.4. Measures Portrayed in ACPs
    4.5. Portrayal of ACPs
    4.6. Databases that Include ACPs
    4.7. Analyses of ACPs with Statistics or Other Quantitative Methods
    4.8. Uses of ACPs
        4.8.1. Use of ACPs to Measure Internal Control
        4.8.2. Use of ACPs to Measure Responses to Environments
        4.8.3. Use of ACPs to Measure Actions on Environments
        4.8.4. Use of ACPs to Fingerprint Individuals
        4.8.5. Use of ACPs to Portray Test Results
        4.8.6. Use of ACPs to Identify Predictors of Disorder
        4.8.7. Use of ACPs to Identify Predictors of Differential Response
        4.8.8. Use of ACPs to Measure Interactions Involving Different Types of Action
        4.8.9. Use of ACPs to Help Distinguish Causal from Non-causal Associations
            4.8.9.1. Exploring for Causal Relationships
            4.8.9.2. Confirming Causal Relationships
        4.8.10. Use of ACPs for Data Mining
        4.8.11. Use of ACPs for Nested Systems
        4.8.12. Use of ACPs to Distinguish Episodes of Action
        4.8.13. Use of ACPs for Model Development and Testing
        4.8.14. Use of ACPs to Draw Generalized Conclusions and to Make Predictions

APPENDIX
Outline of Application 4.8.15. Use of ACPs to Make Scientific Discoveries
    4.8.16. Use of ACPs to Guide Decision-Making
  4.9. Examples of ACPs
5. Appendix

I claim:

1. A method to construct at least one profile representing how actions of an object of investigation are coordinated, the method utilizing a computer or computer system programmed to:

process repeated measures or time series data for two or more variables or sets of variables to form dichotomous series or sets of dichotomous series that show the presence or absence of independent events on each of two or more measurement occasions, each variable or set of variables being used to construct one or more rows or columns for one dimension of an action coordination profile;

process repeated measures or time series data for two or more variables or sets of variables to form dichotomous series or sets of dichotomous series that show the presence or absence of dependent events on each of two or more measurement occasions, each variable or set of variables being used to construct one or more rows or columns for a second dimension of an action coordination profile;

compute values of measures such as longitudinal association scores, benefit/harm scores, measures derived from longitudinal association scores, or summaries of any such scores or measures for cells formed by combining rows and columns for independent and dependent events thereby constructing an action coordination profile or set of action coordination profiles.

2. The method as claimed in claim 1 wherein the same variables or any set or sets of variables are used to construct both dimensions of an action coordination profile or set of action coordination profiles.

3. The method as claimed in claim 1 wherein at least one of the features used to form dichotomous series or sets of dichotomous series that show the presence or absence of independent or dependent events is selected from the group consisting of variable level, episode length, episode criterion, delay, persistence, Boolean events, delay after Boolean events, persistence after Boolean events, transition events, or other procedures used to form additional dichotomous series.

4. The method as claimed in claim 1 wherein an action coordination profile is constructed using longitudinal association scores that quantify the amount of evidence for any association together with the positive or negative direction of any association.

5. The method as claimed in claim 1 wherein an action coordination profile includes benefit/harm scores that quantify benefit/harm of one or more independent variables or any set or sets of independent variables with respect to one or more dependent variables or a set or sets of dependent variables.

6. The method as claimed in claim 1 wherein an action coordination profile is constructed using values of strength of longitudinal association measures that quantify the strength of any association together with the positive or negative direction of any association.

7. The method as claimed in claim 1 wherein an action coordination profile is constructed using a measure that summarizes sets of longitudinal association scores, sets of benefit/harm scores, or sets of strength measures.

8. The method as claimed in claim 1 wherein the action coordination profile or some portion of an action coordination profile is portrayed as a table.

9. The method as claimed in claim 1 wherein the action coordination profile or some portion of an action coordination profile is portrayed as a graph, figure, image, display, or interactive display.

10. The method as claimed in claim 1 wherein the object represented by an action coordination profile is an individual biological system or organism such as a person or some portion of an organism such as a cell, tissue, organ, organ system, or biochemical pathway.

11. The method as claimed in claim 10 in which an action coordination profile is used to investigate protein-protein interactions or predictors of particular types of protein-protein interactions.

12. The method as claimed in claim 10 in which an action coordination profile is used to investigate activity; as measured by devices such as those used for functional magnetic resonance imaging, Positron Emission Tomography, electroencephalography, and electrocardiography; in an organ or biological structure such as a brain or a heart.

13. The method as claimed in claim 1 in which data used to construct an action coordination profile includes data obtained by using biochemical measurement technologies.

14. The method as claimed in claim 1 in which data used to construct an action coordination profile includes data obtained by using MicroElectroMechanical Systems (MEMS).

15. The method as claimed in claim 1 wherein the object represented by an action coordination profile is a population of individuals investigated as a whole.

16. The method as claimed in claim 1 wherein the object represented by an action coordination profile is an ecosystem.

17. The method as claimed in claim 1 wherein the object represented by an action coordination profile is a weather system.

18. The method as claimed in claim 1 wherein the object represented by an action coordination profile is a machine or other type of man made process or system.

19. The method as claimed in claim 1 wherein the object represented by an action coordination profile is an economy or investment market.

20. The method as claimed in claim 1 wherein the object represented by an action coordination profile is a system consisting of two or more individuals that may interact.

21. The method as claimed in claim 1 wherein the object represented by an action coordination profile is a social system.

22. The method as claimed in claim 1 wherein the action is movement.

23. The method as claimed in claim 1 wherein the action is chemical or biochemical.

24. The method as claimed in claim 1 wherein the action is physical or electromagnetic.

25. The method as claimed in claim 1 wherein the action is behavior.

26. The method as claimed in claim 1 wherein the action is performance.

27. The method as claimed in claim 1 wherein the action indicates mental or emotional activity.

28. The method as claimed in claim 1 wherein the data used to construct the action coordination profile include data collected with instrumentation for psychometric, psychophysical, or neuropsychiatric testing or with rating scales or surveys.

29. The method as claimed in claim 1 in which ACPs are applied to the subject matter of chemistry, biology, psychology, sociology, economics, medicine, or combinations thereof.

30. The method as claimed in claim 1 wherein all variables and types of events are considered to be internal to the object being investigated so that the action coordination profile can indicate internal control of dynamic functioning.

31. The method as claimed in claim 1 wherein at least one variable or type of event is considered to be external to an object being investigated so that an action coordination profile includes indicators of how the individual object may affect its environment.

32. The method as claimed in claim 1 wherein at least one variable or type of event is considered to be external to an object being investigated so that an action coordination profile includes indicators of how an environment may affect an individual object.

33. The method as claimed in claim 32 wherein at least one external variable or type of event is a treatment.

34. The method as claimed in claim 1 in which an action coordination profile is constructed by a procedure that includes use of optional values of the analysis parameter called delay, the resulting profile or profiles being used to help evaluate the temporal criterion of causal and other predictive relationships.

35. The method as claimed in claim 1 in which asymmetries between portions of action coordination profiles are used to help evaluate the temporal criterion of causal and other predictive relationships.

36. The method as claimed in claim 1 in which at least some of the data that are processed to construct at least one action coordination profile are collected under experimental conditions to help distinguish causal from non-causal associations.

37. The method as claimed in claim 1 in which action coordination profiles or information derived therefrom is analyzed statistically or with other quantitative methods.

38. The method as claimed in claim 1 wherein action coordination profiles from two or more individuals are used to help identify any predictors of any disordered functioning.

39. The method as claimed in claim 38 in which any disordered functioning is a health disorder.

40. The method as claimed in claim 38 in which any predictors of any disordered functioning are genetic.

41. The method as claimed in claim 1 in which action coordination profiles from two or more individuals are used to help identify any predictors of any differential response to one or more environmental variables or sets of environmental variables.

42. The method as claimed in claim 41 in which at least one environmental variable or set of environmental variables is a treatment.

43. The method as claimed in claim 41 in which any predictors of any differential response are genetic.

44. The method as claimed in claim 1 in which at least one action coordination profile or portion of an action coordination profile is used as part of a test.

45. The method as claimed in claim 1 in which action coordination profiles are used for data mining.

46. The method as claimed in claim 1 in which action coordination profiles are used to investigate nested systems.

47. The method as claimed in claim 1 in which at least one predictive index is used as a variable in computing action coordination profiles.

48. The method as claimed in claim 1 in which action coordination profiles are constructed sequentially or iteratively over measurement occasions.

49. The method as claimed in claim 1 in which action coordination profiles are used to distinguish episodes of action.

50. The method as claimed in claim 1 in which an action coordination profile or set of profiles for an individual or the action coordination profiles for a group, sample, or population of individuals are used to inform the process of creating, refining, or verifying mathematical models.

51. The method as claimed in claim 1 in which an action coordination profile for an individual or the action coordination profiles for a group, sample, or population of individuals are used to draw generalized conclusions.

52. The method as claimed in claim 1 in which an action coordination profile for an individual or the action coordination profiles for a group, sample, or population of individuals are used to make predictions.

53. The method as claimed in claim 1 in which an action coordination profile for an individual or the action coordination profiles for a group, sample, or population of individuals are used to make scientific discoveries.

54. The method as claimed in claim 1 in which an action coordination profile for an individual or the action coordination profiles for a group, sample, or population of individuals are used to guide decision-making.

55. The method as claimed in claim 1 that is implemented, applied, or used on the Internet.

56. A computer or computational system to construct at least one profile representing how the actions of an object of investigation are coordinated, the system comprising:

means to process repeated measures or time series data for two or more variables or sets of variables to form dichotomous series or sets of dichotomous series that show the presence or absence of independent events on each of two or more measurement occasions, each variable or set of variables being used to construct one or more rows or columns for one dimension of an action coordination profile;

means to process repeated measures or time series data for two or more variables or sets of variables to form dichotomous series or sets of dichotomous series that show the presence or absence of dependent events on each of two or more measurement occasions, each variable or set of variables being used to construct one or more rows or columns for a second dimension of an action coordination profile;

means to compute values of measures such as longitudinal association scores, benefit/harm scores, measures derived from longitudinal association scores, or summaries of any such scores or measures for cells formed by combining rows and columns for independent and dependent events thereby constructing an action coordination profile or set of action coordination profiles.

57. The computer or computational system as claimed in claim 56 wherein the same variables or any set or sets of variables are used to construct both dimensions of an action coordination profile or set of action coordination profiles.

58. The computer or computational system as claimed in claim 56 wherein at least one of the features used to form dichotomous series or sets of dichotomous series that show the presence or absence of independent or dependent events is selected from the group consisting of variable level, episode length, episode criterion, delay, persistence, Boolean events, delay after Boolean events, persistence after Boolean events, transition events, or other procedures used to form additional dichotomous series.

59. The computer or computational system as claimed in claim 56 wherein an action coordination profile is constructed using longitudinal association scores that quantify the amount of evidence for any association together with the positive or negative direction of any association.

60. The computer or computational system as claimed in claim 56 wherein an action coordination profile includes benefit/harm scores that quantify benefit/harm of one or more independent variables or any set or sets of independent variables with respect to one or more dependent variables or a set or sets of dependent variables.

61. The computer or computational system as claimed in claim 56 wherein an action coordination profile is constructed using values of strength of longitudinal association measures that quantify the strength of any association together with the positive or negative direction of any association.

62. The computer or computational system as claimed in claim 56 wherein an action coordination profile is constructed using a measure that summarizes sets of longitudinal association scores, sets of benefit/harm scores, or sets of strength measures.

63. The computer or computational system as claimed in claim 56 wherein the action coordination profile or some portion of an action coordination profile is portrayed as a table.

64. The computer or computational system as claimed in claim 56 wherein the action coordination profile or some portion of an action coordination profile is portrayed as a graph, figure, image, display, or interactive display.

65. The computer or computational system as claimed in claim 56 wherein the object represented by an action coordination profile is an individual biological system or organism such as a person or some portion of an organism such as a cell, tissue, organ, organ system, or biochemical pathway.

66. The computer or computational system as claimed in claim 65 in which an action coordination profile is used to investigate protein-protein interactions or predictors of particular types of protein-protein interactions.

67. The computer or computational system as claimed in claim 65 in which an action coordination profile is used to investigate activity; as measured by devices such as those used for functional magnetic resonance imaging, Positron Emission Tomography, electroencephalography, and electrocardiography; in an organ or biological structure such as a brain or a heart.

68. The computer or computational system as claimed in claim 56 in which data used to construct an action coordination profile includes data obtained by using biochemical measurement technologies.

69. The computer or computational system as claimed in claim 56 in which data used to construct an action coordination profile includes data obtained by using MicroElectroMechanical Systems (MEMS).

70. The computer or computational system as claimed in claim 56 wherein the object represented by an action coordination profile is a population of individuals investigated as a whole.

71. The computer or computational system as claimed in claim 56 wherein the object represented by an action coordination profile is an ecosystem.

72. The computer or computational system as claimed in claim 56 wherein the object represented by an action coordination profile is a weather system.

73. The computer or computational system as claimed in claim 56 wherein the object represented by an action coordination profile is a machine or other type of man made process or system.

74. The computer or computational system as claimed in claim 56 wherein the object represented by an action coordination profile is an economy or investment market.

75. The computer or computational system as claimed in claim 56 wherein the object represented by an action coordination profile is a system consisting of two or more individuals that may interact.

76. The computer or computational system as claimed in claim 56 wherein the object represented by an action coordination profile is a social system.

77. The computer or computational system as claimed in claim 56 wherein the action is movement.

78. The computer or computational system as claimed in claim 56 wherein the action is chemical or biochemical.

79. The computer or computational system as claimed in claim 56 wherein the action is physical or electromagnetic.

80. The computer or computational system as claimed in claim 56 wherein the action is behavior.

81. The computer or computational system as claimed in claim 56 wherein the action is performance.

82. The computer or computational system as claimed in claim 56 wherein the action indicates mental or emotional activity.

83. The computer or computational system as claimed in claim 56 wherein the data used to construct the action coordination profile include data collected with instrumentation for psychometric, psychophysical, or neuropsychiatric testing or with rating scales or surveys.

84. The computer or computational system as claimed in claim 56 in which ACPs are applied to the subject matter of chemistry, biology, psychology, sociology, economics, medicine, or combinations thereof.

85. The computer or computational system as claimed in claim 56 wherein all variables and types of events are considered to be internal to the object being investigated so that the action coordination profile can indicate internal control of dynamic functioning.

86. The computer or computational system as claimed in claim 56 wherein at least one variable or type of event is considered to be external to an object being investigated so that an action coordination profile includes indicators of how the individual object may affect its environment.

87. The computer or computational system as claimed in claim 56 wherein at least one variable or type of event is considered to be external to an object being investigated so that an action coordination profile includes indicators of how an environment may affect an individual object.

88. The computer or computational system as claimed in claim 87 wherein at least one external variable or type of event is a treatment.

89. The computer or computational system as claimed in claim 56 in which an action coordination profile is constructed by a procedure that includes use of optional values of the analysis parameter called delay, the resulting profile or profiles being used to help evaluate the temporal criterion of causal and other predictive relationships.

90. The computer or computational system as claimed in claim 56 in which asymmetries between portions of action coordination profiles are used to help evaluate the temporal criterion of causal and other predictive relationships asymmetries between portions of action coordination profiles are used to help evaluate the temporal criterion of causal and other predictive relationships.

91. The computer or computational system as claimed in claim 56 in which at least some of the data that are processed to construct at least one action coordination profile are collected under experimental conditions to help distinguish causal from non-causal associations.

92. A database that includes action coordination profiles or portions of action coordination profiles.

93. The computer or computational system as claimed in claim 56 in which action coordination profiles or information derived therefrom is analyzed statistically or with other quantitative methods.

94. The computer or computational system as claimed in claim 56 wherein action coordination profiles from two or more individuals are used to help identify any predictors of any disordered functioning.

95. The computer or computational system as claimed in claim 94 in which any disordered functioning is a health disorder.

96. The computer or computational system as claimed in claim 94 in which any predictors of any disordered functioning are genetic.

97. The computer or computational system as claimed in claim 56 in which action coordination profiles from two or more individuals are used to help identify any predictors of any differential response to one or more environmental variables or sets of environmental variables.

98. The computer or computational system as claimed in claim 97 in which at least one environmental variable or set of environmental variables is a treatment.

99. The computer or computational system as claimed in claim 97 in which any predictors of any differential response are genetic.

100. The computer or computational system as claimed in claim 56 in which at least one action coordination profile or portion of an action coordination profile is used as part of a test.

101. The computer or computational system as claimed in claim 56 in which action coordination profiles are used for data mining.

102. The computer or computational system as claimed in claim 56 in which action coordination profiles are used to investigate nested systems.

103. The computer or computational system as claimed in claim 56 in which at least one predictive index is used as a variable in computing action coordination profiles.

104. The computer or computational system as claimed in claim 56 in which action coordination profiles are constructed sequentially or iteratively over measurement occasions.

105. The computer or computational system as claimed in claim 56 in which action coordination profiles are used to distinguish episodes of action.

106. The computer or computational system as claimed in claim 56 in which an action coordination profile or set of profiles for an individual or the action coordination profiles for a group, sample, or population of individuals are used to inform the process of creating, refining, or verifying mathematical models.

107. The computer or computational system as claimed in claim 56 in which an action coordination profile for an individual or the action coordination profiles for a group, sample, or population of individuals are used to draw generalized conclusions.

108. The computer or computational system as claimed in claim 56 in which an action coordination profile for an individual or the action coordination profiles for a group, sample, or population of individuals are used to make predictions.

109. The computer or computational system as claimed in claim 56 in which an action coordination profile for an individual or the action coordination profiles for a group, sample, or population of individuals are used to make scientific discoveries.

110. The computer or computational system as claimed in claim 56 in which an action coordination profile for an individual or the action coordination profiles for a group, sample, or population of individuals are used to guide decision-making.

111. The computer or computational system as claimed in claim 56 that is implemented, applied, or used on the Internet.

* * * * *